(12) United States Patent
Makino et al.

(10) Patent No.: US 12,260,553 B2
(45) Date of Patent: Mar. 25, 2025

(54) MOBILE RADIATION GENERATION APPARATUS, METHOD FOR OPERATING MOBILE RADIATION GENERATION APPARATUS, AND OPERATION PROGRAM FOR MOBILE RADIATION GENERATION APPARATUS

(71) Applicant: FUJIFILM CORPORATION, Tokyo (JP)

(72) Inventors: Kazuhiro Makino, Kanagawa (JP); Takeyasu Kobayashi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 380 days.

(21) Appl. No.: 17/822,135

(22) Filed: Aug. 25, 2022

(65) Prior Publication Data

US 2022/0414872 A1 Dec. 29, 2022

Related U.S. Application Data

(63) Continuation of application No. PCT/JP2020/049029, filed on Dec. 25, 2020.

(30) Foreign Application Priority Data

Mar. 30, 2020 (JP) ................................. 2020-061591

(51) Int. Cl.
G06T 7/00 (2017.01)

(52) U.S. Cl.
CPC .. *G06T 7/0012* (2013.01); *G06T 2207/10116* (2013.01)

(58) Field of Classification Search
CPC ........... A61B 6/00; A61B 6/566; A61B 6/563; A61B 6/56; G16H 30/20; G16H 30/40;
(Continued)

(56) References Cited

U.S. PATENT DOCUMENTS

2008/0240357 A1* 10/2008 Jabri .................... A61B 6/5252
378/154
2010/0046705 A1 2/2010 Jabri et al.
(Continued)

FOREIGN PATENT DOCUMENTS

JP 2004-295184 A 10/2004
JP 2008-253758 A 10/2008
(Continued)

OTHER PUBLICATIONS

English language translation of the following: Office action dated Apr. 18, 2023 from the JPO in a Japanese patent application No. 2022-511538 corresponding to the instant patent application.
(Continued)

*Primary Examiner* — Andrae S Allison
*Assistant Examiner* — Emmanuel Silva-Avina
(74) *Attorney, Agent, or Firm* — SOLARIS Intellectual Property Group, PLLC

(57) ABSTRACT

A mobile radiation generation apparatus that is used for a first radiography system configured to capture a first radiographic image, has a radiation generation unit including a radiation tube configured to emit radiation, is movable with a carriage having wheels, and is driven with a battery includes at least one processor configured to execute first reception processing of receiving the first radiographic image, first computer aided diagnosis processing of executing computer aided diagnosis processing on the first radiographic image, second reception processing of receiving a second radiographic image from a second radiography system different from the first radiography system, second computer aided diagnosis processing of executing the computer aided diagnosis processing on the second radiographic image, and return processing of returning a result of the
(Continued)

second computer aided diagnosis processing to the second radiography system.

12 Claims, 21 Drawing Sheets

(58) Field of Classification Search
CPC .................. G16H 50/20; G16H 50/70; G06T 2207/10116; G06T 7/0012
USPC ........................................................ 382/132
See application file for complete search history.

(56) References Cited

U.S. PATENT DOCUMENTS

| | | | |
|---|---|---|---|
| 2010/0177941 A1 | 7/2010 | Shiozawa et al. | |
| 2018/0317870 A1* | 11/2018 | Fehre | A61B 6/4441 |
| 2019/0125306 A1* | 5/2019 | Oh | G16H 50/20 |
| 2019/0150857 A1* | 5/2019 | Nye | G16H 30/40 |
| 2019/0156484 A1 | 5/2019 | Nye et al. | |
| 2019/0164285 A1 | 5/2019 | Nye et al. | |
| 2022/0354447 A1* | 11/2022 | Imamura | A61B 6/465 |

FOREIGN PATENT DOCUMENTS

| | | | |
|---|---|---|---|
| JP | 2010-158482 A | | 7/2010 |
| JP | 2017051420 A | * | 3/2017 |
| JP | 2019-093137 A | | 6/2019 |

OTHER PUBLICATIONS

International Search Report issued in International Application No. PCT/JP2020/049029 on Mar. 16, 2021.
Written Opinion of the ISA issued in International Application No. PCT/JP2020/049029 on Mar. 16, 2021.

* cited by examiner

FIG. 8

| IMAGING MENU 90 | IRRADIATION CONDITION 91 |
|---|---|
| FRONT CHEST DECUBITUS  BODY SHAPE SMALL | TUBE VOLTAGE 150 kV  TUBE CURRENT 20 mA  IRRADIATION TIME 10 ms |
| FRONT CHEST DECUBITUS  BODY SHAPE MEDIUM | TUBE VOLTAGE 150 kV  TUBE CURRENT 25 mA  IRRADIATION TIME 10 ms |
| FRONT CHEST DECUBITUS  BODY SHAPE LARGE | TUBE VOLTAGE 150 kV  TUBE CURRENT 30 mA  IRRADIATION TIME 10 ms |
| ... | ... |

71

MOBILE RADIATION GENERATION APPARATUS, METHOD FOR OPERATING MOBILE RADIATION GENERATION APPARATUS, AND OPERATION PROGRAM FOR MOBILE RADIATION GENERATION APPARATUS

CROSS-REFERENCE TO RELATED APPLICATIONS

This application is a continuation application of International Application No. PCT/JP2020/049029 filed on Dec. 25, 2020, the disclosure of which is incorporated herein by reference in its entirety. Further, this application claims priority from Japanese Patent Application No. 2020-061591 filed on Mar. 30, 2020, the disclosure of which is incorporated herein by reference in its entirety.

BACKGROUND

1. Technical Field

A technique of the present disclosure relates to a mobile radiation generation apparatus, a method for operating a mobile radiation generation apparatus, and an operation program for a mobile radiation generation apparatus.

2. Description of the Related Art

In the medical field, diagnosis using a radiographic image captured with a radiography system has been actively performed. The radiography system comprises a radiation generation apparatus having a radiation tube configured to emit radiation, and a radiographic image detection device that receives radiation transmitted through a subject and outputs a radiographic image.

As the radiation generation apparatus, a mobile radiation generation apparatus is known. The mobile radiation generation apparatus has, for example, a configuration in which a body portion having a radiation generation unit including the radiation tube is mounted on a carriage having wheels, and is movable by the carriage. The mobile radiation generation apparatus can be driven with a battery.

The mobile radiation generation apparatus utilizes mobility and is used in so-called round imaging for imaging a patient as a subject while visiting patient's rooms. Alternatively, the mobile radiation generation apparatus is also used in imaging in an emergency room. Furthermore, the mobile radiation generation apparatus can also be carried in an operation room and used in the middle of an operation. In addition, the mobile radiation generation apparatus can also be carried in an outdoor disaster site and used in emergency. Since the mobile radiation generation apparatus can be driven with the battery, the mobile radiation generation apparatus can be used as in a normal state even though the mobile radiation generation apparatus encounters a failure of a public infrastructure, such as blackout.

JP2008-253758A describes a radiography system in which a mobile radiation generation apparatus has a function of computer aided diagnosis (CAD) processing. With the radiography system described in JP2008-253758A, the CAD processing can be instantly executed on a radiographic image output from the radiographic image detection device with the mobile radiation generation apparatus at an imaging site and a result of the CAD processing can be displayed.

SUMMARY

In the radiography system described in JP2008-253758A, a target of the CAD processing in the mobile radiation generation apparatus is limited to a radiographic image from the radiographic image detection device configuring the system. For this reason, it has been difficult to say that the function of the CAD processing is effectively utilized.

An object of the technique of the present disclosure is to provide a mobile radiation generation apparatus, a method for operating a mobile radiation generation apparatus, and an operation program for a mobile radiation generation apparatus capable of effectively utilizing a function of computer aided diagnosis processing.

To achieve the above-described object, there is provided a mobile radiation generation apparatus of the present disclosure that is used for a first radiography system configured to capture a first radiographic image, has a radiation generation unit including a radiation tube configured to emit radiation, is movable with a carriage having wheels, and is driven with a battery, the mobile radiation generation apparatus comprising at least one processor configured to execute first reception processing of receiving the first radiographic image, first computer aided diagnosis processing of executing computer aided diagnosis processing on the first radiographic image, second reception processing of receiving a second radiographic image from a second radiography system different from the first radiography system, second computer aided diagnosis processing of executing the computer aided diagnosis processing on the second radiographic image, and return processing of returning a result of the second computer aided diagnosis processing to the second radiography system.

It is preferable that the processor is configured to execute first notification processing of notifying the second radiography system that a request for the second computer aided diagnosis processing is acceptable.

It is preferable that the processor is configured to execute erasure processing of erasing the second radiographic image from a storage unit after the return processing.

It is preferable that the processor is configured to execute first restriction processing of bringing the mobile radiation generation apparatus into a state in which only one second radiographic image is present while the second reception processing, the second computer aided diagnosis processing, and the return processing on one second radiographic image are being executed.

It is preferable that the processor is configured to execute second notification processing of notifying the second radiography system that the second reception processing, the second computer aided diagnosis processing, and the return processing on the one second radiographic image are being executed.

It is preferable that a transfer speed at which the second radiographic image received in the second reception processing is transferred to the second computer aided diagnosis processing is faster than a transmission speed of the second radiographic image from the second radiography system.

It is preferable that the processor has a first sub-processor that executes processing other than the first computer aided diagnosis processing and the second computer aided diagnosis processing, and a second sub-processor that executes at least the first computer aided diagnosis processing and the second computer aided diagnosis processing.

It is preferable that the processor is configured to execute second restriction processing of not executing the second computer aided diagnosis processing while imaging-related processing involving imaging of the first radiographic image and including the first reception processing and the first computer aided diagnosis processing is being executed.

It is preferable that the processor is configured to execute third notification processing of notifying the second radiography system that the imaging-related processing is being executed.

It is preferable that the second reception processing and the return processing are processing of receiving and returning the second radiographic image through short range wireless communication or wired communication.

There is provided a method for operating a mobile radiation generation apparatus of the present disclosure that is used for a first radiography system configured to capture a first radiographic image, has a radiation generation unit including a radiation tube configured to emit radiation, is movable with a carriage having wheels, and is driven with a battery, the method causing a processor of a computer to execute first reception processing of receiving the first radiographic image, first computer aided diagnosis processing of executing computer aided diagnosis processing on the first radiographic image, second reception processing of receiving a second radiographic image from a second radiography system different from the first radiography system, second computer aided diagnosis processing of executing the computer aided diagnosis processing on the second radiographic image, and return processing of returning a result of the second computer aided diagnosis processing to the second radiography system.

There is provided an operation program for a mobile radiation generation apparatus of the present disclosure that is used for a first radiography system configured to capture a first radiographic image, has a radiation generation unit including a radiation tube configured to emit radiation, is movable with a carriage having wheels, and is driven with a battery, the operation program causing a processor of a computer to execute first reception processing of receiving the first radiographic image, first computer aided diagnosis processing of executing computer aided diagnosis processing on the first radiographic image, second reception processing of receiving a second radiographic image from a second radiography system different from the first radiography system, second computer aided diagnosis processing of executing the computer aided diagnosis processing on the second radiographic image, and return processing of returning a result of the second computer aided diagnosis processing to the second radiography system.

According to the technique of the present disclosure, it is possible to provide a mobile radiation generation apparatus, a method for operating a mobile radiation generation apparatus, and an operation program for a mobile radiation generation apparatus capable of effectively utilizing a function of computer aided diagnosis processing.

BRIEF DESCRIPTION OF THE DRAWINGS

Exemplary embodiments according to the technique of the present disclosure will be described in detail based on the following figures, wherein:

FIG. 8 is a diagram showing an irradiation condition table;

DETAILED DESCRIPTION

Figure 1:
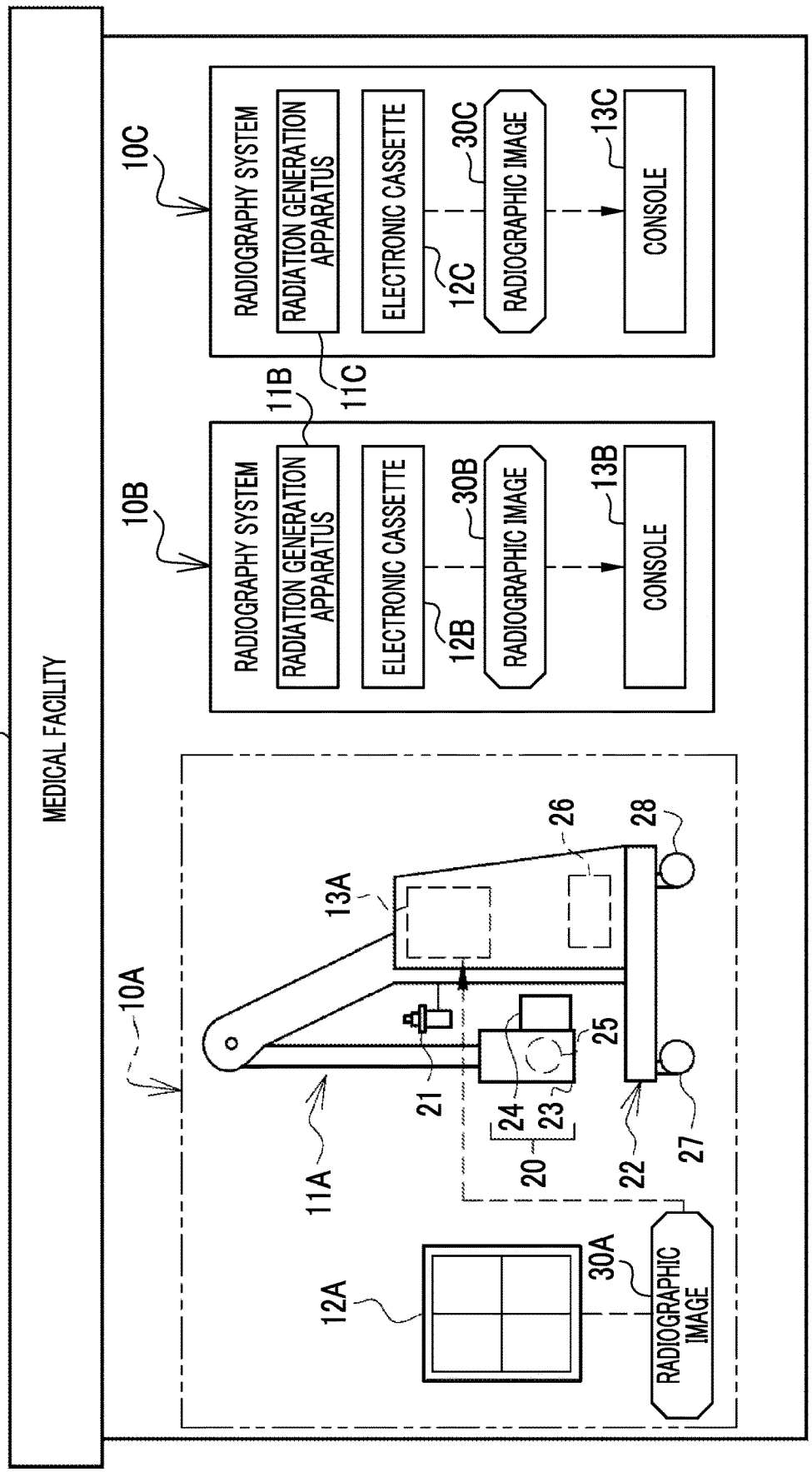
FIG. 1 is a diagram showing a radiography system that is provided in a medical facility.

In FIG. 1, a radiography system 10A, a radiography system 10B, and a radiography system 10C are provided in a medical facility 2. The radiography system 10A comprises a radiation generation apparatus 11A, an electronic cassette 12A, and a console 13A. The console 13A is embedded in the radiation generation apparatus 11A. The radiography system 10B comprises a radiation generation apparatus 11B, an electronic cassette 12B, and a console 13B. Similarly, the radiography system 10C comprises a radiation generation apparatus 11C, an electronic cassette 12C, and a console 13C. The radiography system 10A is an example of a "first radiography system" according to the technique of the present disclosure. The radiography system 10B and the radiography system 10C are an example of a "second radiography system" according to the technique of the present disclosure.

The radiation generation apparatus 11A has a radiation generation unit 20, an irradiation switch 21, and a carriage 22. The radiation generation unit 20 emits radiation R (see FIG. 2) toward a subject H (see FIG. 2). The radiation generation unit 20 is configured with a radiation source 23 and an irradiation field limiter 24. A radiation tube 25 is embedded in the radiation source 23. The radiation tube 25 generates, for example, X-rays as the radiation R.

The irradiation switch 21 is a switch that is provided for an operator OP (see FIG. 2), such as a radiographer, to instruct an irradiation start of the radiation R. The irradiation switch 21 is, for example, a two-stage push switch. The irradiation switch 21 generates a warm-up instruction signal 92 (see FIG. 7) when being pushed to the first stage (half-pushed), and generates an irradiation start instruction signal 93 (see FIG. 7) when being pushed to the second stage (fully pushed).

The radiation tube 25 is provided with a filament, a target, a grid electrode, and the like (all are not shown). A voltage is applied between the filament as a cathode and the target as an anode from a voltage generator 26. The voltage that is applied between the filament and the target is referred to as a tube voltage. The filament discharges thermoelectrons according to the applied tube voltage toward the target. The target radiates radiation R with collision of the thermoelectrons from the filament. The grid electrode is disposed between the filament and the target. The grid electrode changes a flow rate of the thermoelectrons from the filament toward the target according to the voltage applied from the voltage generator 26. The flow rate of the thermoelectrons from the filament toward the target is referred to as a tube current. The tube voltage and the tube current are set as irradiation conditions 91 (see FIGS. 7 and 8) along with an irradiation time.

In a case where the irradiation switch 21 is half-pushed and the warm-up instruction signal 92 is generated, the filament is warmed up and the rotation of the target is started. When the filament reaches a prescribed temperature, and the target reaches a prescribed rotation speed, warm-up is completed. In a case where the irradiation switch 21 is fully pushed and the irradiation start instruction signal 93 is generated in a state in which the warm-up is completed, the tube voltage is applied from the voltage generator 26, and radiation R is generated from the radiation tube 25. When the irradiation time set in the irradiation conditions 91 has elapsed from the start of generation of radiation R, the application of the tube voltage is stopped, and irradiation of radiation R ends.

The irradiation field limiter 24 limits an irradiation field of radiation R generated from the radiation tube 25. For example, the irradiation field limiter 24 has a configuration in which four shield plates formed of lead or the like shielding radiation R are disposed on respective sides of a quadrangle, and an emission opening of the quadrangle transmitting radiation is formed in a center portion. The irradiation field limiter 24 changes the positions of the shield plates to change the size of the emission opening, and accordingly, changes the irradiation field of radiation R.

The carriage 22 has a pair of right and left front wheels 27 and a pair of right and left rear wheels 28. The radiation generation apparatus 11A is movable inside a hospital by the carriage 22. That is, the radiation generation apparatus 11A is an example of a "mobile radiation generation apparatus" according to the technique of the present disclosure. The radiation generation apparatus 11A can be used in so-called round imaging for imaging the subject H while visiting patient's rooms. For this reason, the radiation generation apparatus 11A is also referred to as a treatment cart. The radiation generation apparatus 11A can also be carried to an operation room and used in the middle of an operation. In addition, the radiation generation apparatus 11A can also be carried in an outdoor disaster site and used in emergency.

As well known in the art, the electronic cassette 12A has a sensor panel embedded in a portable housing and is driven by a battery. As is also well known, the sensor panel has a configuration in which a plurality of pixels that are sensitive to the radiation R or visible light converted from the radiation R to generate signal charge are arranged. The electronic cassette 12A receives the radiation R emitted from the radiation generation unit 20 and transmitted through the subject H and outputs a radiographic image 30A. The electronic cassette 12A transmits the radiographic image 30A to the console 13A in a wireless manner. The radiographic image 30A is an example of a "first radiographic image" according to the technique of the present disclosure.

The console 13A receives the radiographic image 30A from the electronic cassette 12A in a wireless manner. The console 13A executes various kinds of image processing on the radiographic image 30A and displays the radiographic image 30A after the image processing on a touch panel display (hereinafter, simply referred to as a display) 42 (see FIG. 4).

The radiation generation apparatus 11B and the radiation generation apparatus 11C emit the radiation R toward the subject H like the radiation generation apparatus 11A. The electronic cassette 12B receives the radiation R transmitted through the subject H and outputs a radiographic image 30B. The electronic cassette 12B transmits the radiographic image 30B to the console 13B in a wireless manner. The electronic cassette 12C receives the radiation R transmitted through the subject H and outputs a radiographic image 30C. The electronic cassette 12C transmits the radiographic image 30C to the console 13C in a wireless manner. The radiographic image 30B and the radiographic image 30C are an example of a "second radiographic image" according to the technique of the present disclosure. Hereinafter, the radiographic image 30A, the radiographic image 30B, and the radiographic image 30C may be collectively written as radiographic images 30. The radiation generation apparatus 11B and the radiation generation apparatus 11C may be a mobile type like the radiation generation apparatus 11A or may be a stationary type that is installed in an imaging room.

The console 13B receives the radiographic image 30B from the electronic cassette 12B in a wireless manner. The console 13B executes various kinds of image processing on the radiographic image 30B and displays the radiographic image 30B after the image processing on a display (not shown). The console 13C receives the radiographic image 30C from the electronic cassette 12C in a wireless manner. The console 13C executes various kinds of image processing on the radiographic image 30C and displays the radiographic image 30C after the image processing on a display (not shown).

Figure 2:
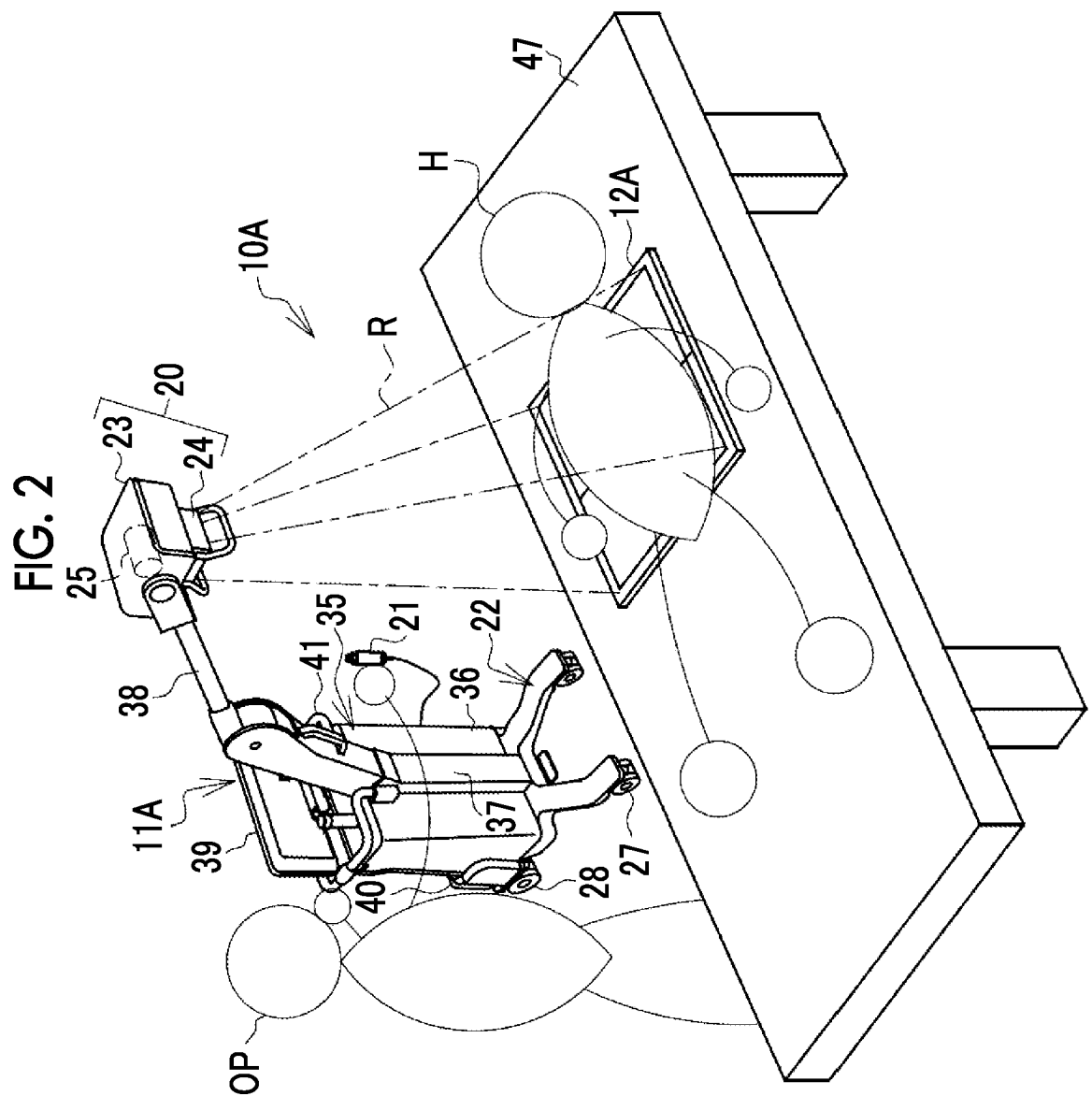
FIG. 2 is a diagram showing a manner of imaging using a radiography system.
Figure 3:
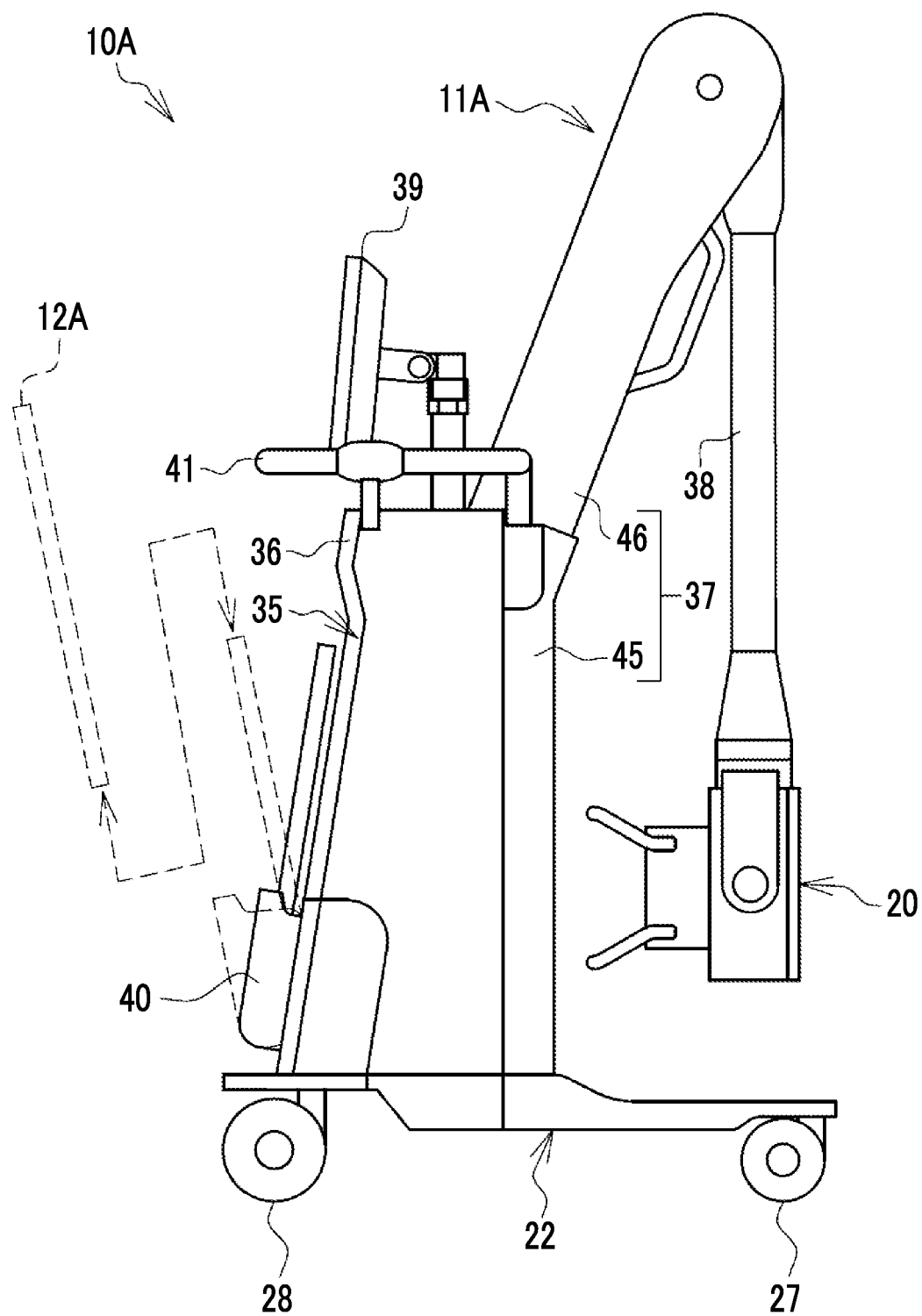
FIG. 3 is a diagram showing the radiography system.

In FIGS. 2 and 3, a body portion 35 is mounted on the carriage 22. The body portion 35 includes a center portion 36, a column portion 37, an arm portion 38, and the like in addition to the above-described radiation generation unit 20.

Figure 4:
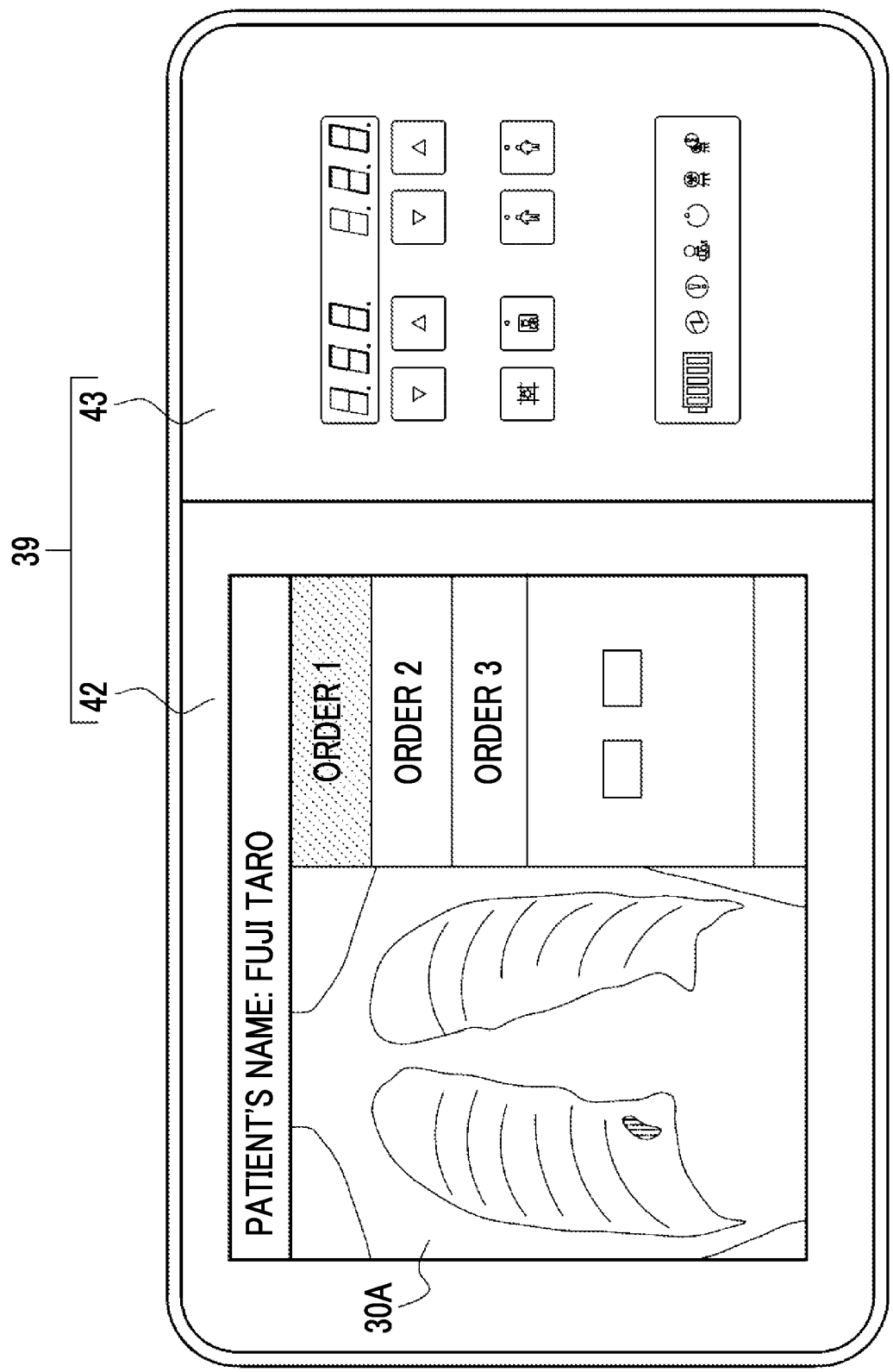
FIG. 4 is a diagram showing a UI-based device.

The center portion 36 has a user interface (UI)-based device 39, a cassette storage portion 40, and a handle 41. As shown in FIG. 4, the UI-based device 39 is configured with a touch panel display 42 and an operation panel 43. The display 42 displays the radiographic image 30A and the like.

The operation panel 43 is operated by the operator OP at the time of setting the irradiation conditions 91 of the radiation R, or the like.

The cassette storage portion 40 is provided on a rear portion side of the center portion 36. The cassette storage portion 40 stores the electronic cassette 12A. There are a plurality of kinds of electronic cassettes 12A having a longitudinal/lateral size of 17 inches×17 inches, 17 inches× 14 inches, 12 inches×10 inches, and the like. The cassette storage portion 40 can store a plurality of kinds of electronic cassettes 12A regardless of the kinds. The cassette storage portion 40 has a function of charging a battery of the stored electronic cassette 12A.

The handle 41 is provided to surround above the center portion 36. The handle 41 is held by the operator OP to operate not only the carriage 22 but also the radiation generation apparatus 11A. The operator OP runs the radiation generation apparatus 11A while holding the handle 41 in a state shown in FIG. 3 in which the radiation generation unit 20 is stored above the carriage 22 and in front of the center portion 36.

The irradiation switch 21 is attached to the center portion 36. An extension cable is connected to the irradiation switch 21, and can be detached from the center portion 36 for use.

The column portion 37 has a prismatic columnar shape and is provided upright at the center of the carriage 22. The arm portion 38 has a base end that is attached to the column portion 37, and a distal end that is a free end on an opposite side to the base end and to which the radiation generation unit 20 is attached.

The column portion 37 has a first column 45 and a second column 46 that is consecutively provided upward at a predetermined angle from the first column 45. The first column 45 is provided on an upper surface of the carriage 22. The second column 46 can rotate with respect to the first column 45 with a vertical axis as a rotation axis.

The arm portion 38 can be bent with respect to the second column 46 or can extend in a direction along the second column 46. The radiation generation unit 20 can swing front and back with respect to the arm portion 38. FIG. 2 shows a manner of imaging a chest of the subject H who lies on a bed 47.

Figure 5:
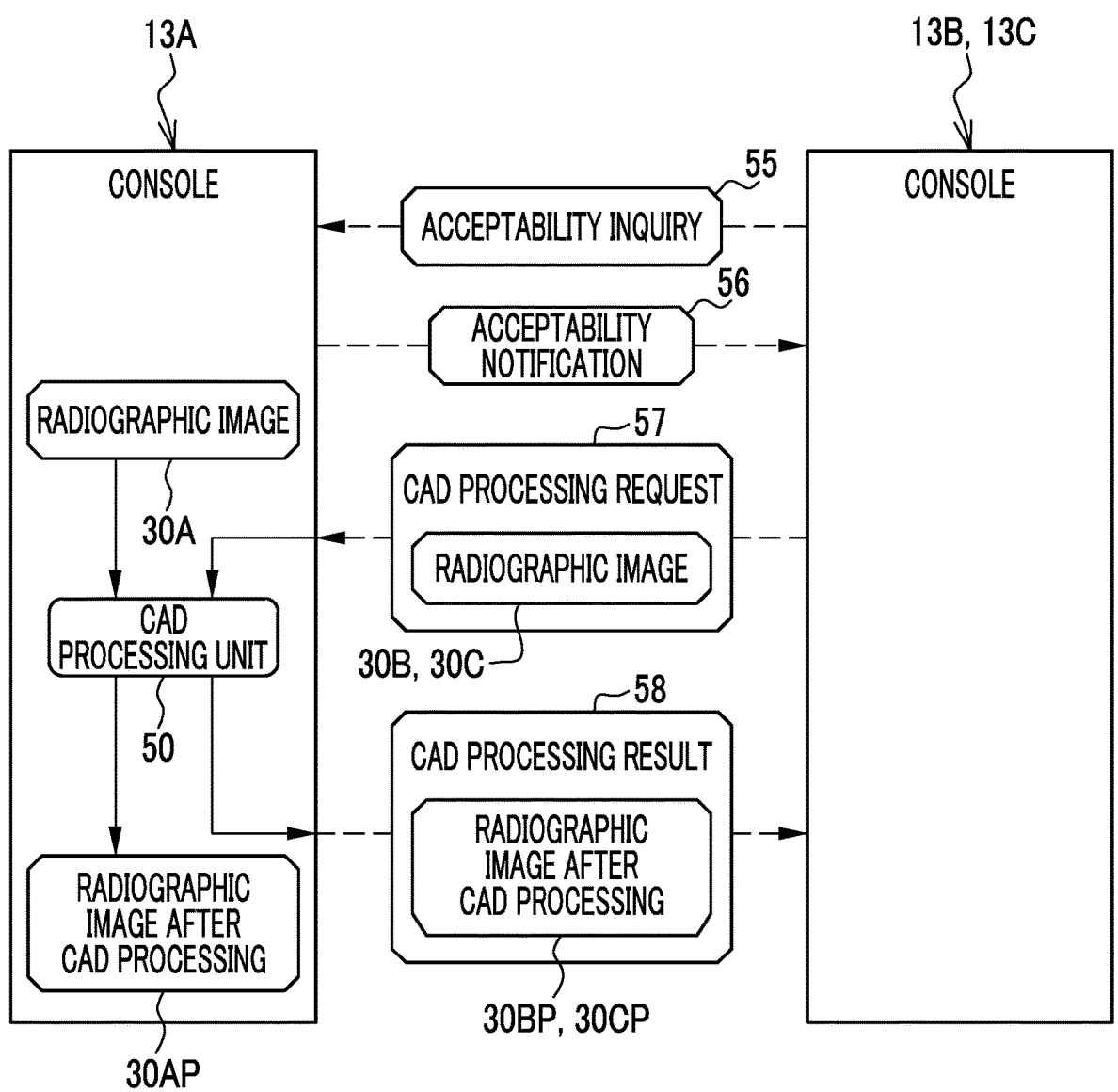
FIG. 5 is a diagram showing various kinds of information that are transmitted between a console having a function of CAD processing and a console having no function of CAD processing.

As shown in FIG. 5, the console 13A has a CAD processing unit 50. The CAD processing unit 50 executes CAD processing on the radiographic image 30A to generate a radiographic image 30AP after the CAD processing. The CAD processing is, for example, processing of extracting a candidate of a lesion, such as a tumor, reflected in the radiographic image 30A. On the other hand, the console 13B and the console 13C do not have a function of the CAD processing.

The console 13B or the console 13C transmits an acceptability inquiry 55 in a wireless manner. The acceptability inquiry 55 inquires of whether or not there is an apparatus that can accept a request for the CAD processing on the radiographic image 30B or the radiographic image 30C. In a case where the acceptability inquiry 55 is received in a wireless manner, the console 13A transmits an acceptability notification 56 to the console 13B or the console 13C in a wireless manner. The acceptability notification 56 is a notification indicating that the console 13A can accept the request for the CAD processing on the radiographic image 30B or the radiographic image 30C. The console 13A receives a CAD processing request 57 transmitted from the console 13B or the console 13C in a wireless manner with respect to the acceptability notification 56. The CAD processing request 57 includes the radiographic image 30B or the radiographic image 30C. The CAD processing request 57 also includes identification information (not shown) of the console 13B or the console 13C, or the like.

The console 13A executes the CAD processing on the radiographic image 30B or the radiographic image 30C in response to the CAD processing request 57 to generate a radiographic image 30BP after the CAD processing or a radiographic image 30CP after the CAD processing. The console 13A transmits a CAD processing result 58 including the radiographic image 30BP after the CAD processing or the radiographic image 30CP after the CAD processing to the console 13B or the console 13C in a wireless manner. In this way, the console 13A executes the CAD processing on the radiographic image 30B or the radiographic image 30C on behalf of the console 13B or the console 13C having no CAD processing function and returns the CAD processing result 58 to the console 13B or the console 13C. The CAD processing result 58 is an example of "a result of second computer aided diagnosis processing" according to the technique of the present disclosure. Hereinafter, the radiographic image 30AP after the CAD processing, the radiographic image 30BP after the CAD processing, and the radiographic image 30CP after the CAD processing may be collectively written as radiographic images 30P after the CAD processing.

Figure 6:
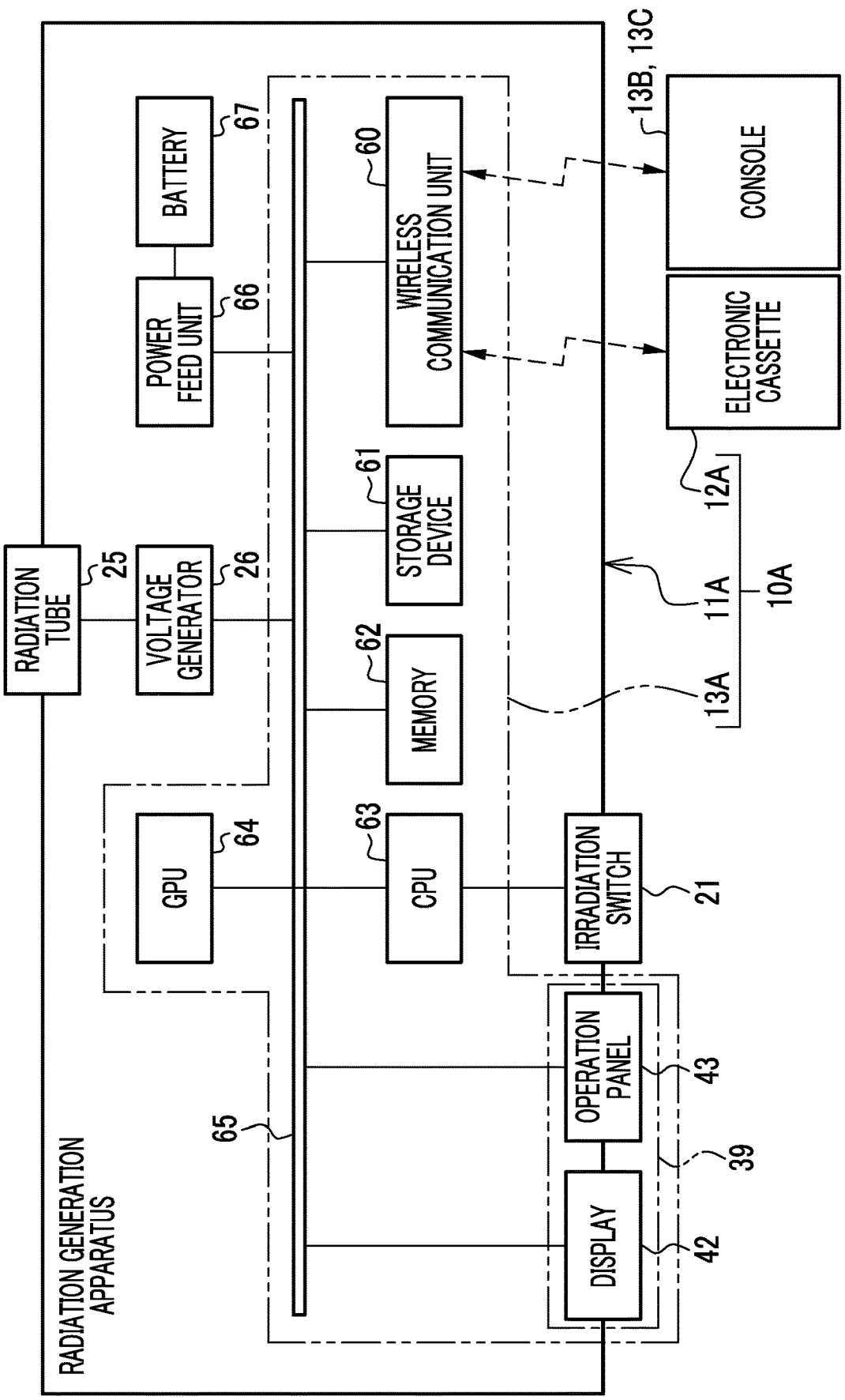
FIG. 6 is a block diagram of a radiation generation apparatus.

In FIG. 6, the radiation generation apparatus 11A has a wireless communication unit 60, a storage device 61, a memory 62, a central processing unit (CPU) 63, a graphics processing unit (GPU) 64, and the like. The wireless communication unit 60, the storage device 61, the memory 62, the CPU 63, the GPU 64, and the like are connected through a busline 65. The voltage generator 26 and the UI-based device 39 are also connected to the busline 65. The wireless communication unit 60, the storage device 61, the memory 62, the CPU 63, the GPU 64, and the busline 65, and the UI-based device 39 configure the console 13A. The storage device 61, the memory 62, the CPU 63, the GPU 64, and the busline 65 are an example of a "computer" according to the technique of the present disclosure. The CPU 63 and the GPU 64 are an example of a "processor" according to the technique of the present disclosure. The GPU 64 may not be included in the configuration of the console 13A and may be connected to the busline 65 or may be included in a configuration dedicated to CAD processing independent of the console 13A.

The wireless communication unit 60 performs wireless communication directly with the electronic cassette 12A. The wireless communication unit 60 performs wireless communication with an external device other than the electronic cassette 12A through a network. Examples of the external device include the console 13B and the console 13C. Examples of the external device include a radiology information system (RIS) that manages information, such as an imaging order, and a picture archiving and communication systems (PACS). Examples of the network include a wide area network (WAN), such as the Internet or a public communication network.

The storage device 61 is, for example, a hard disk drive or a solid state drive, and is an example of a "storage unit" according to the technique of the present disclosure. The storage device 61 stores various programs and various kinds of data associated with various programs. The memory 62 is a work memory on which the CPU 63 or the GPU 64 executes processing. The CPU 63 and the GPU 64 read out a program stored in the storage device 61 to the memory 62 and execute processing depending on the read-out program.

The above-described irradiation switch 21 is connected to the CPU 63. The irradiation switch 21 outputs the warm-up instruction signal 92 and the irradiation start instruction signal 93 to the CPU 63.

A power feed unit 66 is connected to the busline 65. The power feed unit 66 supplies power from the battery 67 to each unit of the radiation generation apparatus 11A. The power feed unit 66 includes a direct-current (DC)-DC converter that converts a direct-current voltage from the battery 67 to a voltage having a value depending on a supply destination, a voltage stabilization circuit that stabilizes the value of the converted voltage, and the like. The battery 67 is embedded in, for example, the center portion 36. In this way, the radiation generation apparatus 11A is driven by the battery 67. The radiation generation apparatus 11A can connect a plug (not shown) of a power cord extending from a lower portion of the body portion 35 to a socket of a commercial power supply to charge the battery 67 or can operate with electric power from the commercial power supply. Alternatively, a charger having a connector that is directly connected to the body portion 35 can also be connected to the body portion 35 to charge the battery 67.

Figure 7:
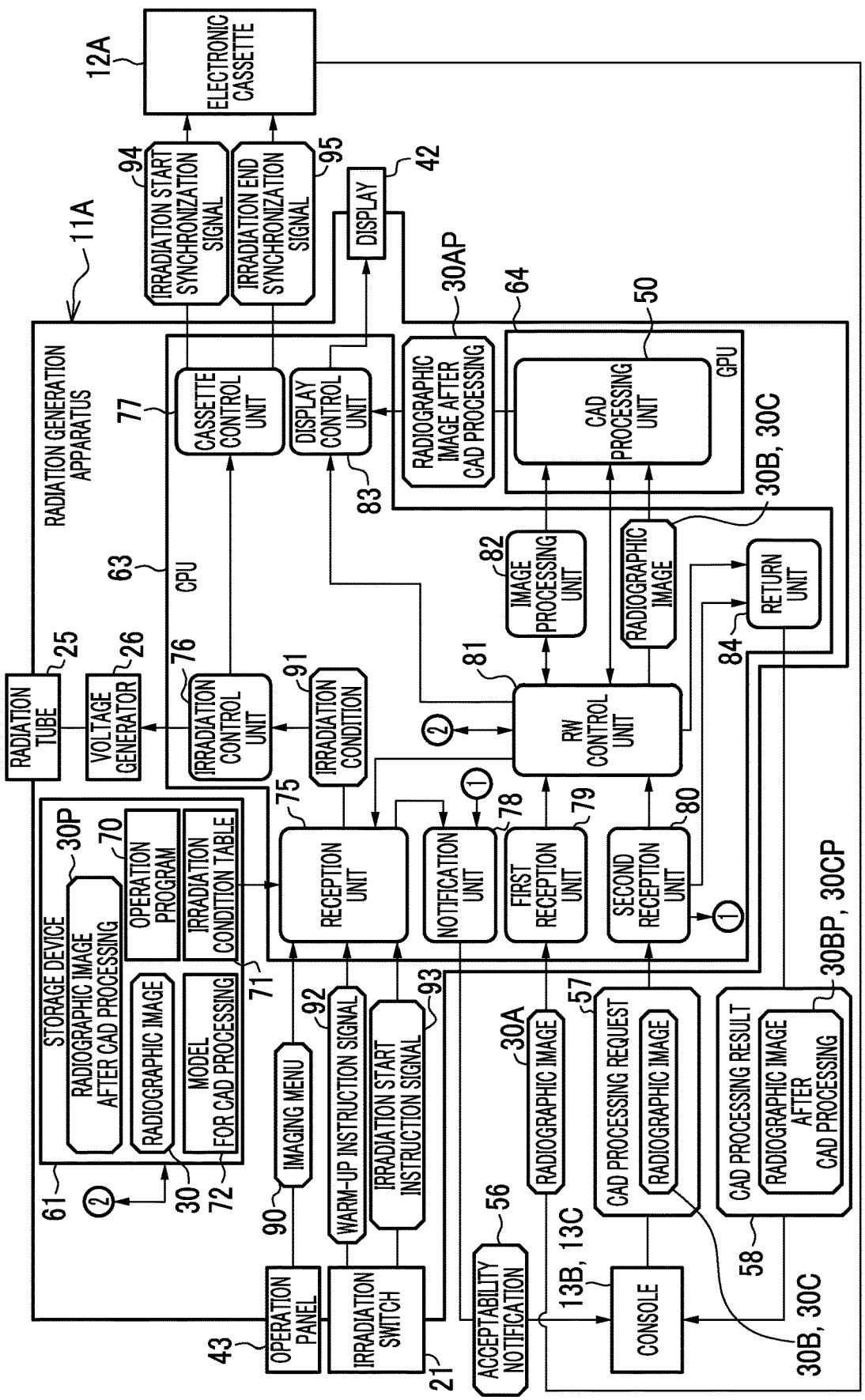
FIG. 7 is a block diagram showing functions of a CPU of the radiation generation apparatus.

In FIG. 7, an operation program 70 is stored in the storage device 61. The operation program 70 is a program causing a computer configured with the storage device 61, the memory 62, the CPU 63, the GPU 64, and the busline 65 to operate as a "mobile radiation generation apparatus" according to the technique of the present disclosure. That is, the operation program 70 is an example of "an operation program for a mobile radiation generation apparatus" according to the technique of the present disclosure. The storage device 61 also stores an irradiation condition table 71 and a model 72 for CAD processing.

The CPU 63 executes the operation program 70 to function as a reception unit 75, an irradiation control unit 76, a cassette control unit 77, a notification unit 78, a first reception unit 79, a second reception unit 80, a read-write (hereinafter, abbreviated as RW) control unit 81, an image processing unit 82, a display control unit 83, and a return unit 84 in cooperation with the memory 62 and the like. The GPU 64 executes the operation program 70 to function as the above-described CAD processing unit 50 in cooperation with the memory 62 and the like. For this reason, the CPU 63 is an example of a "first sub-processor" according to the technique of the present disclosure, and the GPU 64 is an example of a "second sub-processor" according to the technique of the present disclosure.

The reception unit 75 receives an imaging menu 90 input from the operator OP through the operation panel 43. The reception unit 75 reads out the irradiation conditions 91 corresponding to the received imaging menu 90 from the irradiation condition table 71 and outputs the read-out irradiation conditions 91 to the irradiation control unit 76.

The reception unit 75 also receives the warm-up instruction signal 92 and the irradiation start instruction signal 93 from the irradiation switch 21. The reception unit 75 outputs the reception of the warm-up instruction signal 92 to the irradiation control unit 76 and the notification unit 78. The reception unit 75 outputs the reception of the irradiation start instruction signal 93 to the irradiation control unit 76.

The irradiation control unit 76 controls the operation of the radiation tube 25 to control the irradiation of the radiation R. The irradiation control unit 76 sets the irradiation conditions 91 in the voltage generator 26. The irradiation control unit 76 makes the radiation tube 25 perform warm-up in a case where the reception of the warm-up instruction signal 92 is input from the reception unit 75. Furthermore, the irradiation control unit 76 causes the irradiation of the radiation R from the radiation tube 25 through the voltage generator 26 under the set irradiation conditions 91 in a case where the reception of the irradiation start instruction signal 93 is input from the reception unit 75.

The irradiation control unit 76 outputs the start of the irradiation of the radiation R to the cassette control unit 77 conforming to an irradiation start timing of the radiation R. Furthermore, the irradiation control unit 76 outputs the end of the irradiation of the radiation R to the cassette control unit 77 conforming to an irradiation end timing of the radiation R.

The cassette control unit 77 transmits various control signals to the electronic cassette 12A to control the operation of the electronic cassette 12A. The cassette control unit 77 transmits an irradiation start synchronization signal 94 to the electronic cassette 12A in a case where the start of the irradiation of the radiation R is input from the irradiation control unit 76. Furthermore, the cassette control unit 77 transmits an irradiation end synchronization signal 95 to the electronic cassette 12A in a case where the end of the irradiation of the radiation R is input from the irradiation control unit 76. Though not shown, the cassette control unit 77 transmits a gain value and the like of signal charge depending on the irradiation conditions 91 to the electronic cassette 12A.

The notification unit 78 receives the acceptability inquiry 55 from the console 13B or the console 13C (not shown). In a case where the acceptability inquiry 55 is received, the notification unit 78 notifies the console 13B and the console 13C of the acceptability notification 56. That is, the notification unit 78 executes first notification processing of notifying the radiography system 10B and the radiography system 10C that a request for second CAD processing on the radiographic image 30B or the radiographic image 30C can be accepted.

The first reception unit 79 executes first reception processing of receiving the radiographic image 30A from the electronic cassette 12A. The first reception unit 79 outputs the radiographic image 30A to the RW control unit 81.

The second reception unit 80 executes second reception processing of receiving the radiographic image 30B from the console 13B or the radiographic image 30C from the console 13C. Specifically, the second reception unit 80 receives the CAD processing request 57 including the radiographic image 30B or the radiographic image 30C. The second reception unit 80 outputs the radiographic image 30B or the radiographic image 30C to the RW control unit 81. The second reception unit 80 outputs the reception of the CAD processing request 57 to the notification unit 78. In addition, the second reception unit 80 outputs the identification information of the console 13B or the console 13C included in the CAD processing request 57 to the return unit 84.

The RW control unit 81 controls storage of various kinds of data in the storage device 61 and readout of various kinds of data in the storage device 61. The RW control unit 81 reads out the irradiation condition table 71 from the storage device 61 and outputs the irradiation condition table 71 to the reception unit 75. The RW control unit 81 reads out the model 72 for CAD processing from the storage device 61 and outputs the model 72 for CAD processing to the CAD processing unit 50.

The RW control unit 81 stores the radiographic image 30A from the first reception unit 79 in the storage device 61. The RW control unit 81 reads out the radiographic image 30A from the storage device 61 and outputs the radiographic image 30A to the image processing unit 82.

The RW control unit 81 stores the radiographic image 30B or the radiographic image 30C from the second reception unit 80 in the storage device 61. The RW control unit 81 reads out the radiographic image 30B or the radiographic image 30C from the storage device 61 and outputs the radiographic image 30B or the radiographic image 30C to the CAD processing unit 50.

The image processing unit 82 executes image processing of processing the radiographic image 30A to a radiographic image for display. Specifically, the image processing unit 82 executes offset correction processing, sensitivity correction processing, defective pixel correction processing, and the like as the image processing. The offset correction processing is processing of subtracting, from the radiographic image 30A, an offset correction image detected in a state in which there is no irradiation of the radiation R, in units of pixels. The image processing unit 82 executes the offset correction processing to remove fixed pattern noise due to dark charge or the like from the radiographic image 30A. The sensitivity correction processing is processing of correcting variation or the like in sensitivity of each pixel, variation in output characteristic of a circuit that reads out the signal charge, and the like based on sensitivity correction data. The defective pixel correction processing is processing of linearly interpolating a pixel value of a defective pixel with a pixel value of a surrounding normal pixel based on information of a defective pixel having an abnormal pixel value generated during shipment, during a periodic inspection, or the like. The offset correction processing, the sensitivity correction processing, and the defective pixel correction processing are processing essential for making the image quality of the radiographic image 30A enough to endure display. The image processing unit 82 outputs the radiographic image 30A subjected to various image processing described above to the RW control unit 81. The RW control unit 81 stores the radiographic image 30A subjected to the image processing in the storage device 61.

The CAD processing unit 50 executes the CAD processing using the model 72 for CAD processing. The model 72 for CAD processing is a machine learning model that has the radiographic image 30 as input data and the radiographic image 30P after the CAD processing as output data. The model 72 for CAD processing is a learned model where the accuracy of the CAD processing is increased to a predetermined level by learning.

The CAD processing unit 50 receives the radiographic image 30A subjected to the image processing from the RW control unit 81. The CAD processing unit 50 executes first CAD processing of executing the CAD processing on the radiographic image 30A subjected to the image processing to generate the radiographic image 30AP after the CAD processing. The CAD processing unit 50 outputs the radiographic image 30AP after the CAD processing to the RW control unit 81. The RW control unit 81 stores the radiographic image 30AP after the CAD processing in the storage device 61.

The CAD processing unit 50 receives the radiographic image 30B or the radiographic image 30C from the RW control unit 81. The CAD processing unit 50 executes second CAD processing of executing the CAD processing on the radiographic image 30B or the radiographic image 30C to generate the radiographic image 30BP after the CAD processing or the radiographic image 30CP after the CAD processing. The CAD processing unit 50 outputs the radiographic image 30BP after the CAD processing or the radiographic image 30CP after the CAD processing to the RW control unit 81. The RW control unit 81 stores the radiographic image 30BP after the CAD processing or the radiographic image 30CP after the CAD processing in the storage device 61.

As shown in FIG. 4, the display control unit 83 performs control such that the radiographic image 30A is displayed on the display 42. The display control unit 83 performs control for receiving the radiographic image 30AP after the CAD processing from the RW control unit 81 and displaying the radiographic image 30AP after the CAD processing on the display 42 (see FIG. 10).

The return unit 84 receives the radiographic image 30BP after the CAD processing or the radiographic image 30CP after the CAD processing from the RW control unit 81. The return unit 84 executes return processing of returning the CAD processing result 58 including the radiographic image 30BP after the CAD processing to the console 13B or return processing of returning the CAD processing result 58 including the radiographic image 30CP after the CAD processing to the console 13C. The return unit 84 specifies a console to which the CAD processing result 58 is returned, based on the identification information of the console 13B or the console 13C from the second reception unit 80.

As shown in FIG. 8, in the irradiation condition table 71, the irradiation conditions 91 corresponding to various imaging menus 90 are registered. The imaging menu 90 defines an imaging procedure having a set of an imaging part, a posture, and an imaging direction, such as "front chest decubitus". The imaging part is a head, a neck, an abdomen, a waist, a shoulder, an elbow, a hand, a knee, an ankle, and the like in addition to the chest. The posture is an upright posture, a sitting posture, and the like in addition to the decubitus posture. The imaging direction is a rear surface, a lateral surface, and the like in addition to the front surface. Information regarding a body shape of the subject H, such as "body shape small", is also included in the imaging menu 90. As described above, the irradiation conditions 91 are a set of a tube voltage, a tube current, and an irradiation time. Instead of the tube current and the irradiation time, a tube current and irradiation time product may be set as the irradiation condition 91.

The radiation generation apparatus 11A receives an imaging order from the RIS through the wireless communication unit 60. In the imaging order, identification data (ID) for identifying the subject H, instruction information of an imaging procedure by a treatment department physician or the like who issues the imaging order, and the like are registered. The radiation generation apparatus 11A displays the imaging order from the RIS on the display 42 in response to an operation of the operator OP. The operator OP confirms the content of the imaging order through the display 42.

The radiation generation apparatus 11A displays one of a plurality of electronic cassettes 12A stored in the cassette storage portion 40 on the display 42 in a selectable form. The operator OP selects one electronic cassette 12A that is used to image the subject H indicated by the imaging order. With this, the selected electronic cassette 12A and the imaging order are associated with each other.

The radiation generation apparatus 11A displays the imaging menu 90 on the display 42 in a selectable form. The operator OP selects the imaging menu 90 that coincides with the imaging procedure designated by the imaging order and coincides with the body shape of the subject H. With this, the imaging menu 90 is received by the reception unit 75, and the irradiation conditions 91 corresponding to the imaging menu 90 are read out from the irradiation condition table 71 to the reception unit 75. As a result, the irradiation conditions 91 are set in the voltage generator 26 by the irradiation control unit 76. The irradiation conditions 91 read out from the irradiation condition table 71 can be finely adjusted by the operator OP through the operation panel 43 before being set in the voltage generator 26.

Figure 9:
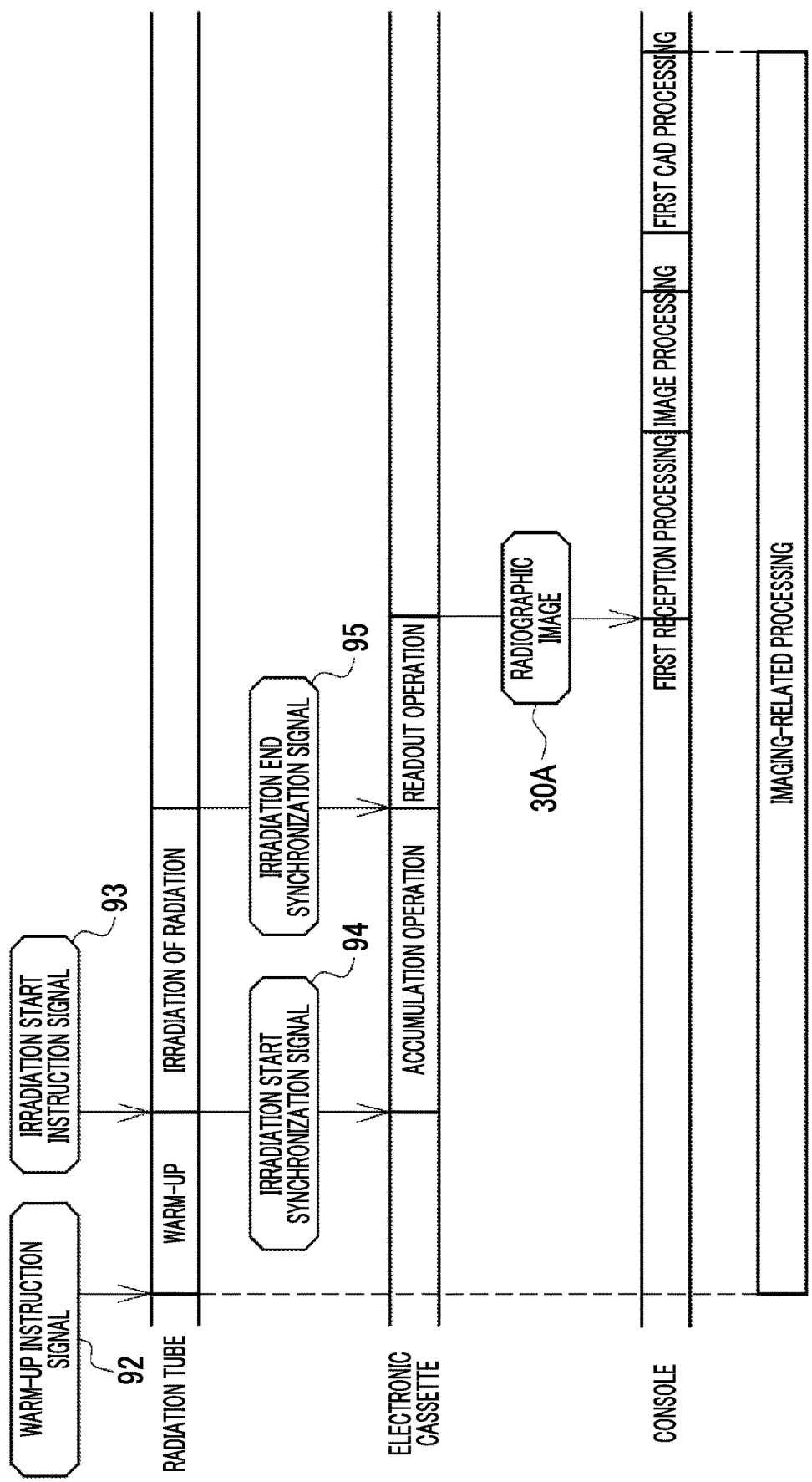
FIG. 9 is a diagram showing imaging-related processing.

As shown in FIG. 9, the radiation tube 25 performs warm-up conforming to the warm-up instruction signal 92 received in the reception unit 75. Next, the radiation tube 25 generates the radiation R conforming to the irradiation start instruction signal 93 received in the reception unit 75. The electronic cassette 12A performs an accumulation operation to make the pixels accumulate the signal charge in response to the irradiation start synchronization signal 94 transmitted conforming to the irradiation start timing of the radiation R after performing a reset operation (not shown) to read out and discard dark charge from the pixels of the sensor panel. Furthermore, the electronic cassette 12A performs a readout operation to read out the signal charge accumulated in the pixels and to output the signal charge as the radiographic image 30A in response to the irradiation end synchronization signal 95 transmitted conforming to the irradiation end timing of the radiation R. The electronic cassette 12A transmits the radiographic image 30A to the console 13A.

The console 13A executes the first reception processing of receiving the radiographic image 30A with the first reception unit 79. The console 13A executes the image processing on the radiographic image 30A with the image processing unit 82. The console 13A displays the radiographic image 30A after the image processing on the display 42 under the control of the display control unit 83. In a case where a set time has elapsed after the radiographic image 30A is displayed on the display 42, the console 13A executes the first CAD processing on the radiographic image 30A with the CAD processing unit 50. The set time is, for example, one minute. The console 13A displays the radiographic image 30A after the CAD processing on the display 42 under the control of the display control unit 83. The series of processing from when the warm-up instruction signal 92 is received in the reception unit 75 in this way to when the first CAD processing on the radiographic image 30A by the CAD processing unit 50 ends is defined as "imaging-related processing" according to the technique of the present disclosure.

Figure 10:
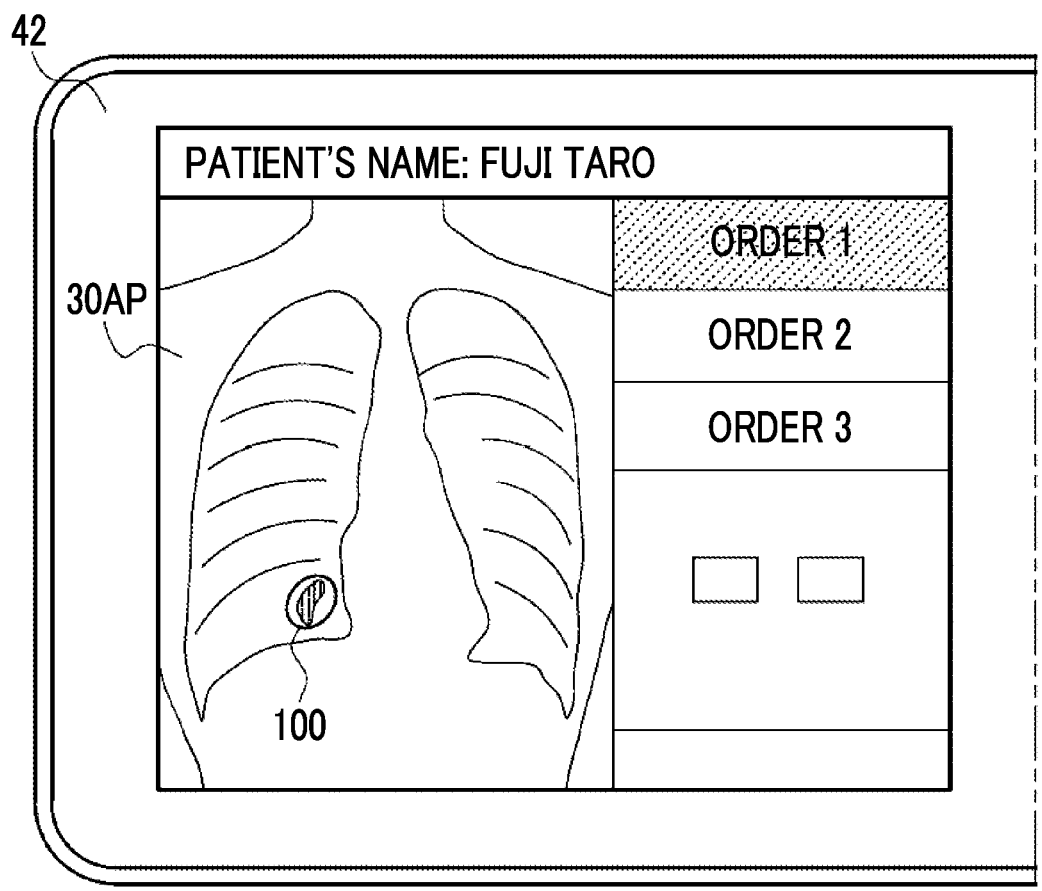
FIG. 10 is a diagram showing a radiographic image after CAD processing.

As shown in FIG. 10, the radiographic image 30AP after the CAD processing is, for example, an image in which a marker 100 surrounding a candidate of a lesion extracted by the first CAD processing is displayed.

In the console 13B or the console 13C, an application program that requests second CAD processing on the radiographic image 30B or the radiographic image 30C to the radiation generation apparatus 11A is installed. The acceptability inquiry 55 is transmitted toward the console 13A in a wireless manner in a case where the application program is activated by an operator of the radiography system 10B or the radiography system 10C.

Figure 11:
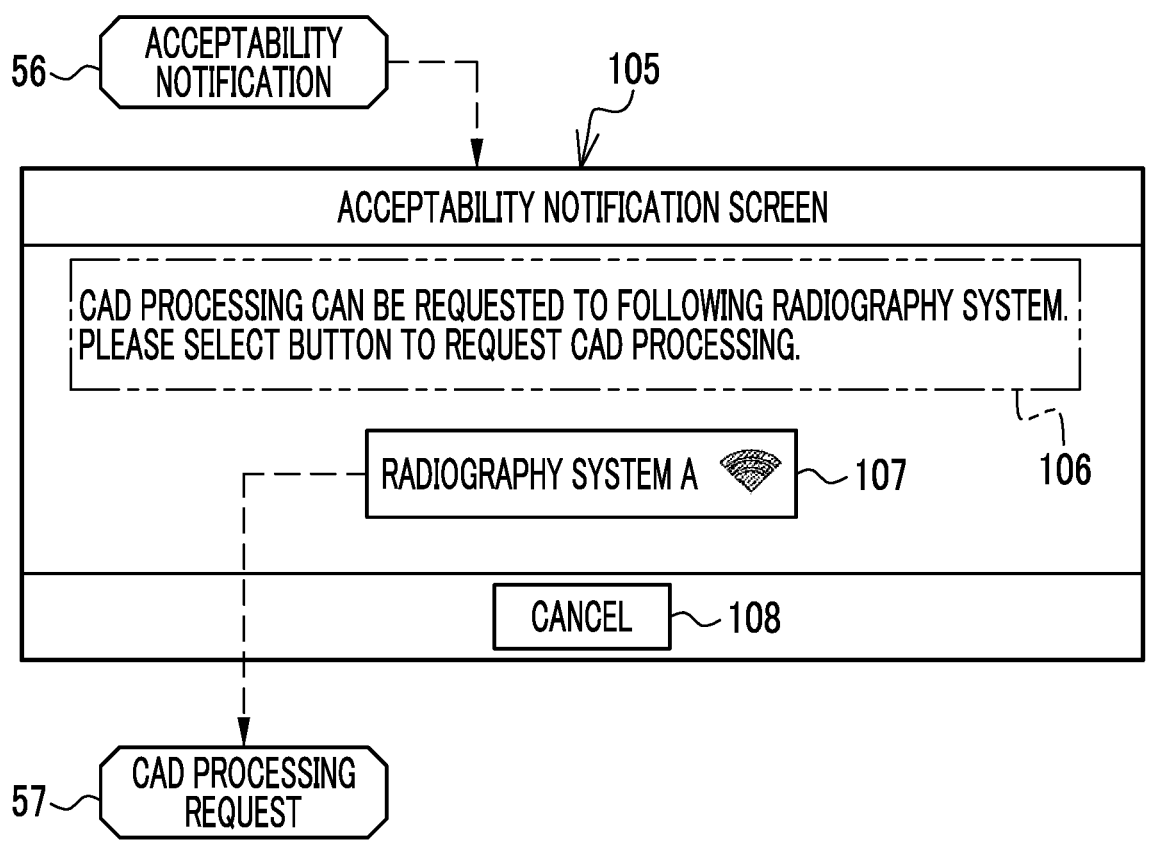
FIG. 11 is a diagram showing an acceptability notification screen.

In a case where the acceptability notification 56 in response to on the acceptability inquiry 55 is received in a wireless manner, the console 13B or the console 13C displays an acceptability notification screen 105 shown in FIG. 11 on the display. On the acceptability notification screen 105, a request button 107 and a cancel button 108 are displayed along with a message 106 indicating that the second CAD processing of the radiographic image 30B or the radiographic image 30C can be requested to the radiography system 10A. In a case where the request button 107 is selected, the CAD processing request 57 is transmitted from the console 13B or the console 13C to the radiation generation apparatus 11A in a wireless manner. In a case where the cancel button 108 is selected, the display of the acceptability notification screen 105 disappears.

Figure 12:
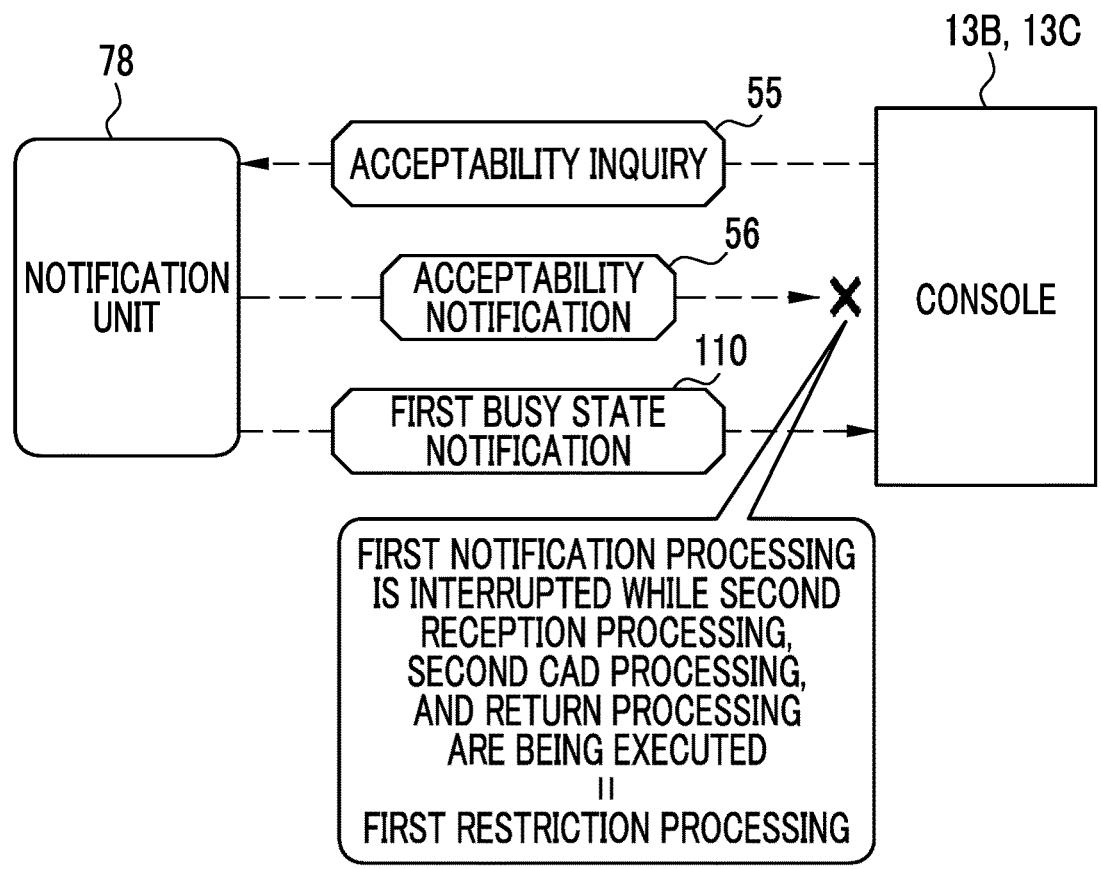
FIG. 12 is a diagram showing a manner of interrupting first notification processing while second reception processing, second CAD processing, and return processing are being executed.

As shown in FIG. 12, the notification unit 78 does not notify of the acceptability notification 56 in response to the acceptability inquiry 55 while the second reception processing, the second CAD processing, the return processing on any one of the radiographic image 30B or the radiographic image 30C are being executed. That is, the notification unit 78 interrupts the first notification processing while the second reception processing, the second CAD processing, and the return processing on any one of the radiographic image 30B or the radiographic image 30C are being executed. For this reason, until the CAD processing request 57 of one "second radiographic image" is received in the second reception unit 80 (second reception processing), and the CAD processing result 58 of the "second radiographic image" is returned from the return unit 84 (return processing), the acceptability notification screen 105 is not displayed in the console 13B and the console 13C. The first notification processing is interrupted in this way, whereby only one "second radiographic image" is present in the radiation generation apparatus 11A while the second reception processing, the second CAD processing, and the return processing are being executed. In other words, two or more "second radiographic images" are not present together in the radiation generation apparatus 11A while the second reception processing, the second CAD processing, and the return processing are being executed. The processing of interrupting the first notification processing shown in FIG. 12 is an example of "first restriction processing" according to the technique of the present disclosure.

The notification unit 78 notifies the console 13B or the console 13C of a first busy state notification 110 instead of the acceptability notification 56. The first busy state notification 110 is a notification indicating that the second reception processing, the second CAD processing, and the return processing on any one of the radiographic image 30B or the radiographic image 30C are being executed in the radiation generation apparatus 11A. That is, the processing of notifying of the first busy state notification 110 is an example of "second notification processing" according to the technique of the present disclosure.

Figure 13:
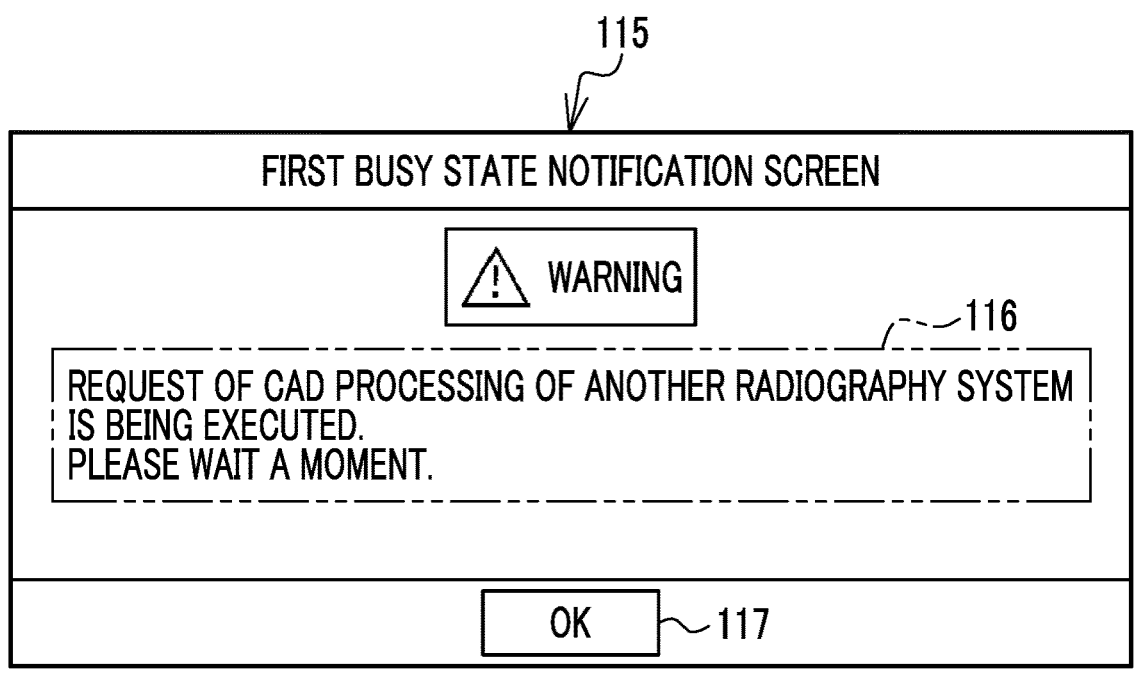
FIG. 13 is a diagram showing a first busy state notification screen.

In a case where the first busy state notification 110 is received, the console 13B or the console 13C displays a first busy state notification screen 115 shown in FIG. 13 on the display. On the first busy state notification screen 115, a message 116 indicating that the request of the second CAD processing on the radiographic image 30B or the radiographic image 30C is being executed in the radiography system 10A is displayed. The display of the first busy state notification screen 115 disappears in a case where an OK button 117 is selected.

Figure 14:
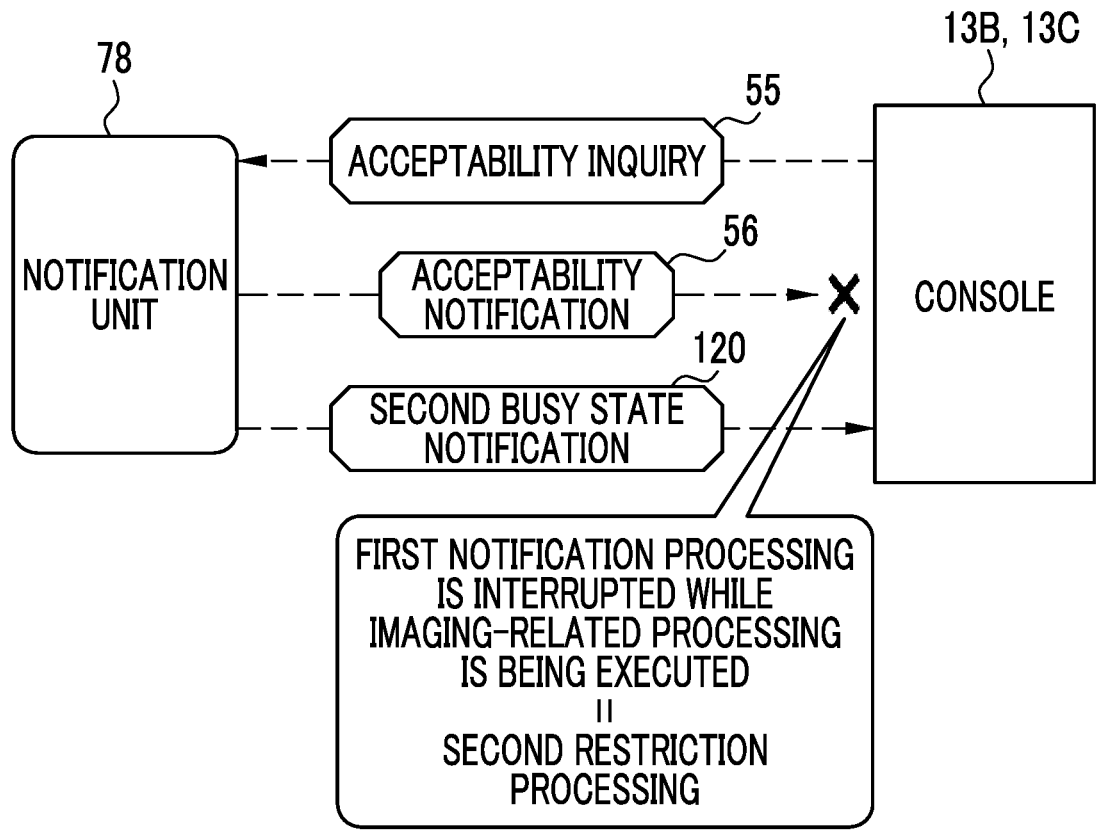
FIG. 14 is a diagram showing a manner of interrupting first notification processing while the imaging-related processing is being executed.

As shown in FIG. 14, the notification unit 78 does not notify of the acceptability notification 56 in response to the acceptability inquiry 55 while the imaging-related processing is being executed. That is, the notification unit 78 interrupts the first notification processing while the imaging-related processing is being executed. For this reason, from when the warm-up instruction signal 92 is received in the reception unit 75 to when the first CAD processing on the radiographic image 30A by the CAD processing unit 50 ends, the acceptability notification screen 105 is not displayed on the console 13B and the console 13C. The first notification processing is interrupted in this way, whereby the radiation generation apparatus 11A does not execute the second reception processing, the second CAD processing, and the return processing while the imaging-related processing is being executed. The processing of interrupting the first notification processing shown in FIG. 13 is an example of "second restriction processing" according to the technique of the present disclosure.

The notification unit 78 notifies the console 13B or the console 13C of a second busy state notification 120 instead of the acceptability notification 56. The second busy state notification 120 is a notification indicating that the imaging-related processing is being executed in the radiation generation apparatus 11A. That is, the processing of notifying of the second busy state notification 120 is an example of "third notification processing" according to the technique of the present disclosure.

Figure 15:
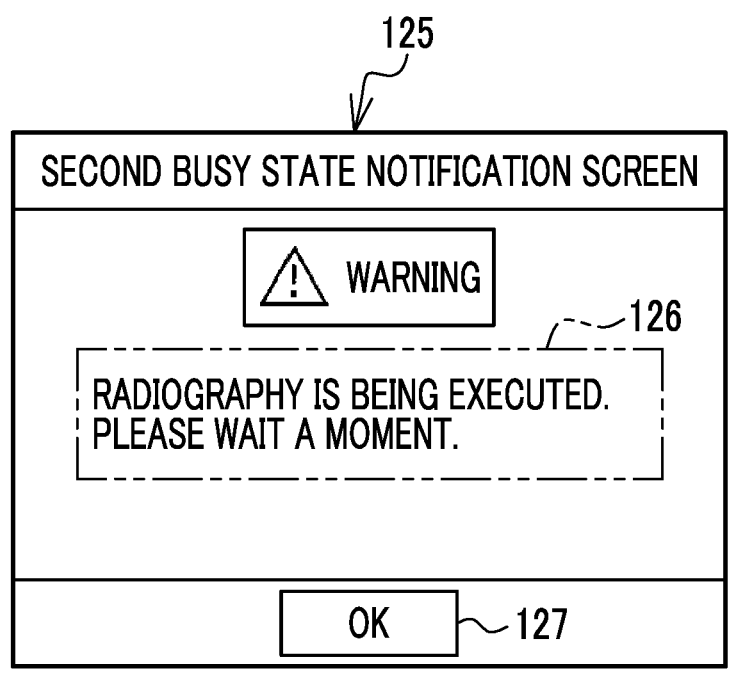
FIG. 15 is a diagram showing a second busy state notification screen.

In a case where the second busy state notification 120 is received, the console 13B or the console 13C displays a second busy state notification screen 125 shown in FIG. 15 on the display. On the second busy state notification screen 125, a message 126 indicating that the imaging-related processing is being executed in the radiography system 10A is displayed. The display of the second busy state notification screen 125 disappears in a case where an OK button 127 is selected.

Figure 16:
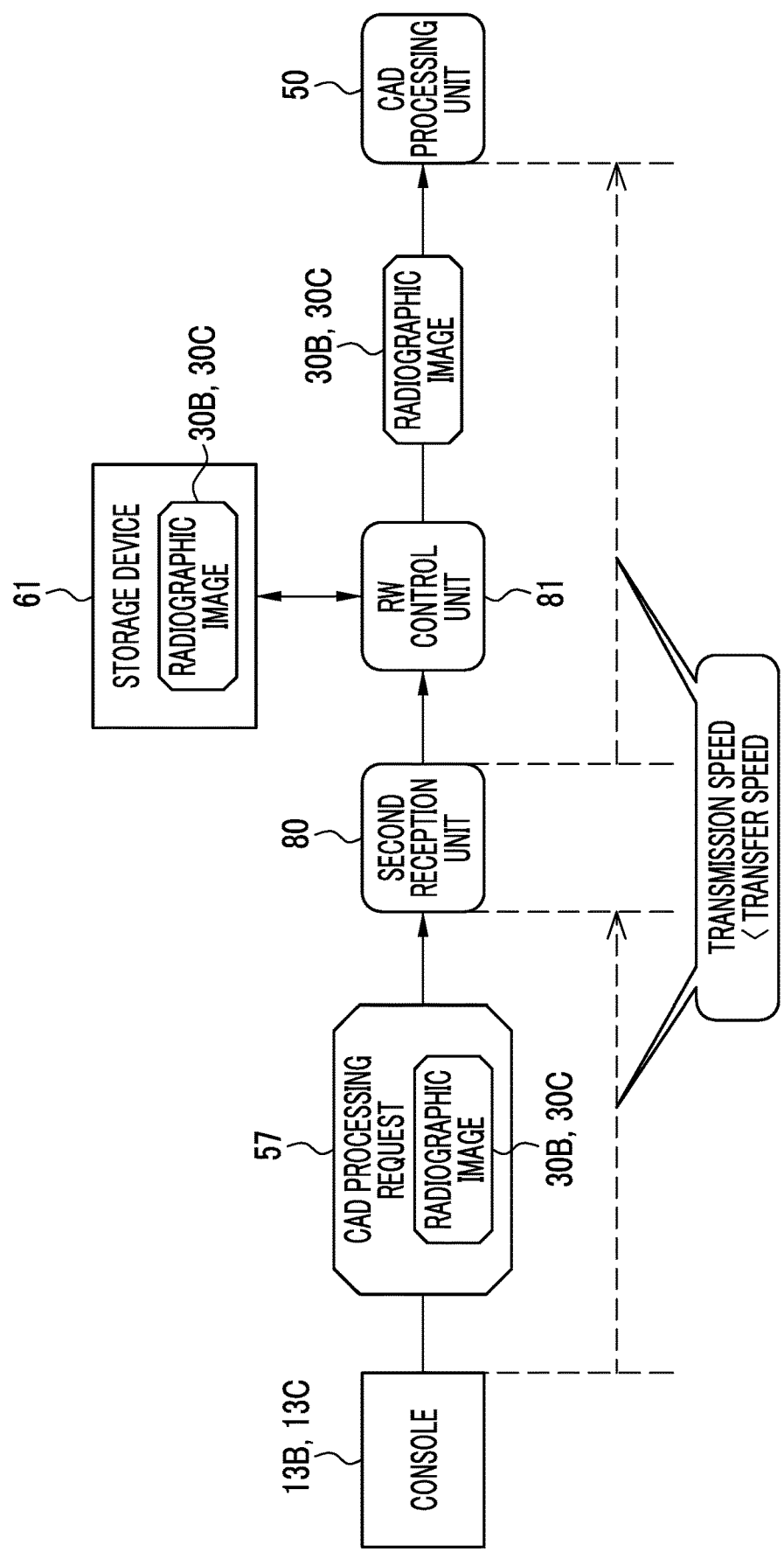
FIG. 16 is a diagram showing a relationship between a transfer speed at which a second radiographic image received in second reception processing is transferred from a second reception unit to a CAD processing unit and a transmission speed of the second radiographic image.

FIG. 16 shows a relationship between a transfer speed and a transmission speed. The transfer speed is a speed at which the radiographic image 30B or the radiographic image 30C received in the second reception processing is transferred from the second reception unit 80 to the CAD processing unit 50 by way of the RW control unit 81. The transmission speed is a speed at which the CAD processing request 57 is transmitted from the console 13B or the console 13C to the second reception unit 80. That is, the transmission speed is a speed at which the radiographic image 30B is transmitted from the console 13B to the second reception unit 80 and a speed at which the radiographic image 30C is transmitted from the console 13C to the second reception unit 80. As shown in a balloon in a lower portion, the transfer speed is faster than the transmission speed.

Figure 17:
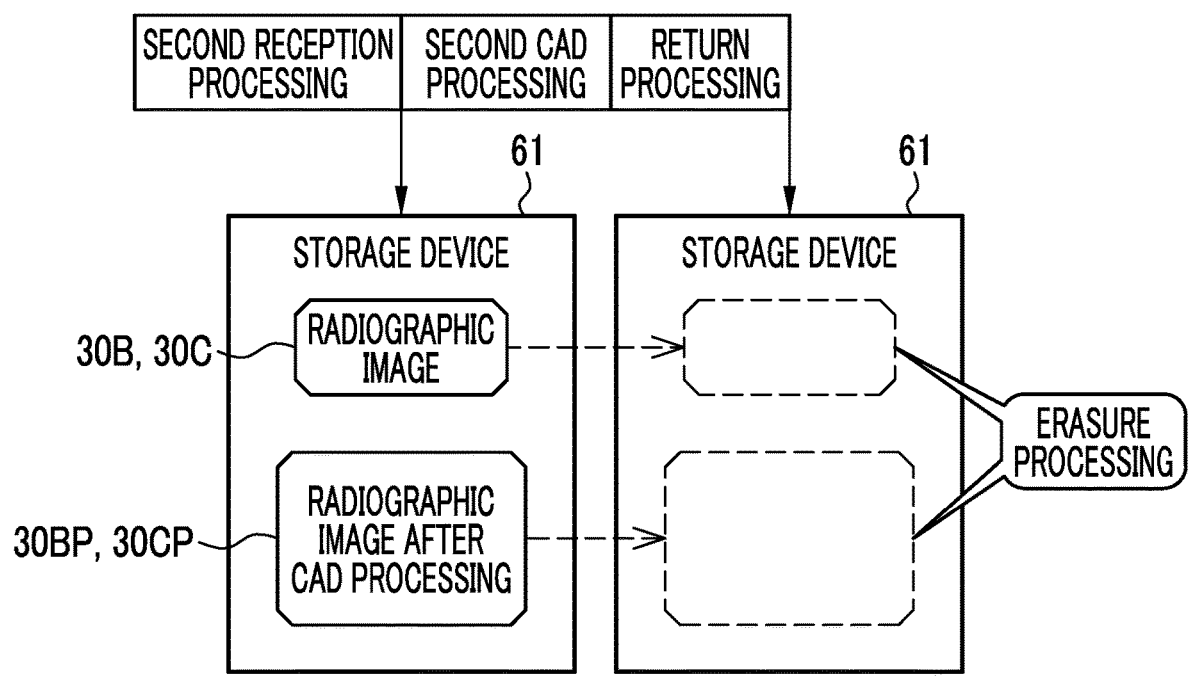
FIG. 17 is a diagram showing a manner of erasure processing of erasing the second radiographic image from a storage device after the return processing.

As shown in FIG. 17, the RW control unit 81 executes processing of erasing the radiographic image 30B or the radiographic image 30C from the storage device 61 after the return processing of the CAD processing result 58 by the return unit 84. Similarly, the RW control unit 81 executes erasure processing of erasing the radiographic image 30BP after the CAD processing or the radiographic image 30CP after the CAD processing from the storage device 61.

The RW control unit 81 stores an execution history of the second CAD processing in the storage device 61. The execution history of the second CAD processing includes, for example, a time at which the CAD processing request 57 is received in the second reception unit 80, the identification of the console 13B or the console 13C as a transmission source of the CAD processing request 57, identification information of the radiographic image 30B or the radiographic image 30C included in the CAD processing request 57, and a time at which the second CAD processing is executed.

Next, the operations of the above-described configuration will be described referring to flowcharts of FIGS. 18 and 19. In a case where the operation program 70 is activated, as shown in FIG. 7, the CPU 63 functions as the reception unit 75, the irradiation control unit 76, the cassette control unit 77, the notification unit 78, the first reception unit 79, the second reception unit 80, the RW control unit 81, the image processing unit 82, the display control unit 83, and the return unit 84. The GPU 64 functions as the CAD processing unit 50.

Before imaging, the imaging menu 90 corresponding to the imaging order is selected by the operator OP through the display 42, and the imaging menu 90 is received in the reception unit 75. Then, the irradiation conditions 91 corresponding to the imaging menu 90 are read out from the irradiation condition table 71 by the reception unit 75. The read-out irradiation conditions 91 are finely adjusted by the operator OP as needed, and then, are set in the voltage generator 26 by the irradiation control unit 76.

Figure 18:
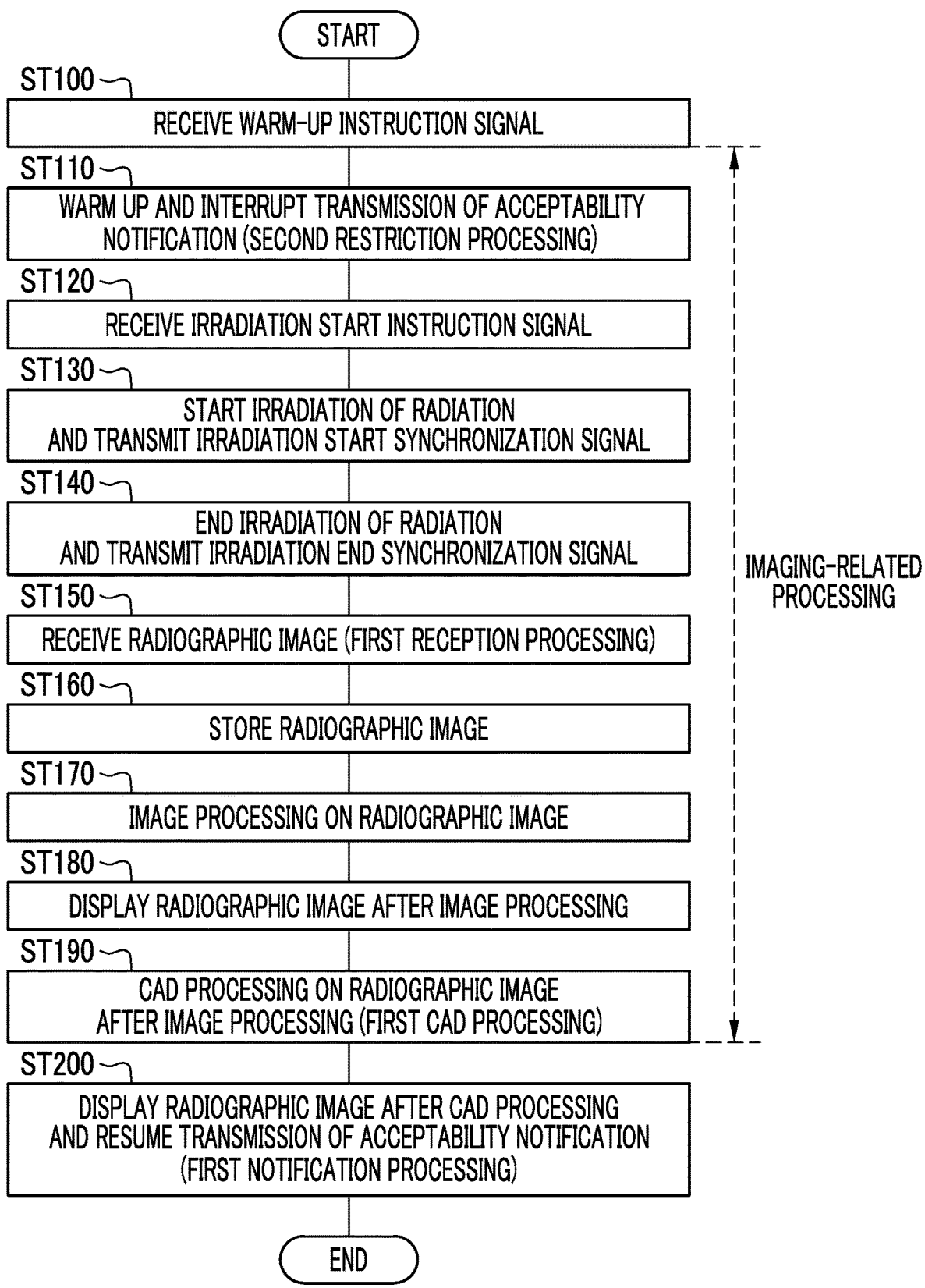
FIG. 18 is a diagram showing a processing procedure of the radiation generation apparatus.

In FIG. 18, after the irradiation conditions 91 are set, the irradiation switch 21 is operated by the operator OP, and the warm-up instruction signal 92 is received in the reception unit 75 (Step ST100). With this, as shown in FIG. 9, the radiation tube 25 is warmed up (Step ST110). As shown in FIG. 14, wireless transmission (first notification processing) of the acceptability notification 56 by the notification unit 78 in response to the acceptability inquiry 55 is interrupted (Step ST110, the second restriction processing).

After the warm-up, the irradiation switch 21 is further operated by the operator OP, and the irradiation start instruction signal 93 is received in the reception unit 75 (Step ST120). With this, as shown in FIG. 9, the irradiation of the radiation R is started from the radiation tube 25 under the set irradiation conditions 91, and the irradiation start synchronization signal 94 is transmitted from the cassette control unit 77 to the electronic cassette 12A (Step ST130). In the electronic cassette 12A, the accumulation operation is performed in response to the irradiation start synchronization signal 94.

After the irradiation time set in the irradiation conditions 91 has elapsed, the irradiation of the radiation R from the radiation tube 25 ends, and the irradiation end synchronization signal 95 is transmitted from the cassette control unit 77 to the electronic cassette 12A (Step ST140). In the electronic cassette 12A, the read-out operation is performed in response to the irradiation end synchronization signal 95. With this, the radiographic image 30A is output from the electronic cassette 12A.

The radiographic image 30A from the electronic cassette 12A is received by the first reception unit 79 (Step ST150, the first reception processing). The radiographic image 30A is output from the first reception unit 79 to the RW control unit 81 and is stored in the storage device 61 by the RW control unit 81 (Step ST160).

The radiographic image 30A is read out from the storage device 61 by the RW control unit 81 and is output to the image processing unit 82. Then, in the image processing unit 82, various kinds of image processing, such as offset correction processing, sensitivity correction processing, and defective pixel correction processing, are executed on the radiographic image 30A (Step ST170). The radiographic image 30A after the image processing is output from the image processing unit 82 to the RW control unit 81 and is stored in the storage device 61 by the RW control unit 81.

As shown in FIG. 4, the radiographic image 30A after the image processing is displayed on the display 42 by the display control unit 83 (Step ST180). With this, the operator OP can instantly confirm a reflected state of the radiographic image 30A at an imaging site.

When the set time has elapsed after the radiographic image 30A is displayed on the display 42, the CAD processing is executed on the radiographic image 30A after the image processing by the CAD processing unit 50 (Step ST190, the first CAD processing). With this, the radiographic image 30A is changed to the radiographic image 30AP after the CAD processing. The radiographic image 30AP after the CAD processing is output from the CAD processing unit 50 to the RW control unit 81 and is stored in the storage device 61 by the RW control unit 81.

In a case where the warm-up instruction signal 92 is received in the reception unit 75 (Step ST100), the imaging-related processing is started. Then, in a case where the first CAD processing on the radiographic image 30A by the CAD processing unit 50 ends (Step ST190), the imaging-related processing ends.

While the imaging-related processing is being executed, in a case where the acceptability inquiry 55 is received, as shown in FIG. 14, the second busy state notification 120, instead of the acceptability notification 56, is notified from the notification unit 78 to the console 13B or the console 13C. With the reception of the second busy state notification 120, the second busy state notification screen 125 shown in FIG. 15 is displayed on the display of the console 13B or the console 13C.

As shown in FIG. 10, the radiographic image 30AP after the CAD processing is displayed on the display 42 by the display control unit 83 (Step ST200). Wireless transmission (the first notification processing) of the acceptability notification 56 by the notification unit 78 in response to the acceptability inquiry 55 is resumed (Step ST200). The radiographic image 30AP after the CAD processing is displayed on the display 42, whereby the operator OP can instantly confirm the radiographic image 30AP after the CAD processing at the imaging site.

The operator of the radiography system 10B or the radiography system 10C activates the application program for requesting the second CAD processing on the radiographic image 30B or the radiographic image 30C to the radiation generation apparatus 11A. With this, the acceptability inquiry 55 is transmitted from the console 13B or the console 13C to the console 13A in a wireless manner.

Figure 19:
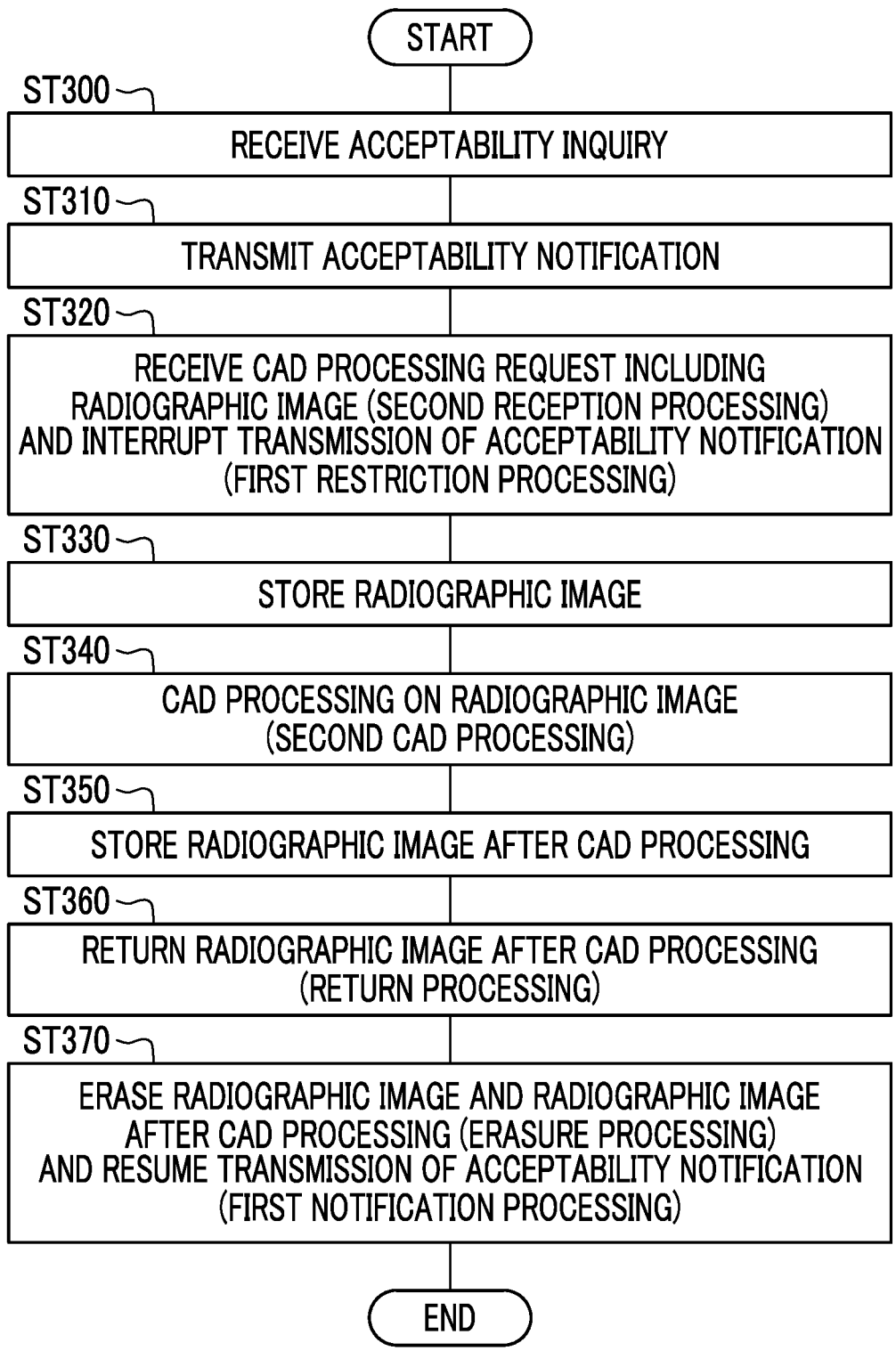
FIG. 19 is a diagram showing a processing procedure of the radiation generation apparatus.

As shown in FIG. 19, the acceptability inquiry 55 is received by the notification unit 78 (Step ST300). After the acceptability inquiry 55 is received, the acceptability notification 56 is transmitted from the notification unit 78 (Step ST310, the first notification processing).

With the reception of the acceptability notification 56, the acceptability notification screen 105 shown in FIG. 11 is displayed on the display of the console 13B or the console 13C. In a case where the request button 107 is selected on the acceptability notification screen 105, the CAD processing request 57 including the radiographic image 30B or the CAD processing request 57 including the radiographic image 30C is transmitted from the console 13B or the console 13C to the console 13A in a wireless manner.

The CAD processing request 57 is received by the second reception unit 80 (Step ST320, the second reception processing). As shown in FIG. 12, wireless transmission (the first notification processing) of the acceptability notification 56 by the notification unit 78 is interrupted (Step ST320, the first restriction processing). The radiographic image 30B or the radiographic image 30C included in the CAD processing request 57 is output from the second reception unit 80 to the RW control unit 81 and is stored in the storage device 61 by the RW control unit 81 (Step ST330).

The radiographic image 30B or the radiographic image 30C is read out from the storage device 61 by the RW control unit 81 and is output to the CAD processing unit 50. Then, the CAD processing is executed on the radiographic image 30B or the radiographic image 30C by the CAD processing unit 50 (Step ST340, the second CAD processing). With this, the radiographic image 30B is changed to the radiographic image 30BP after the CAD processing or the radiographic image 30C is changed to the radiographic image 30CP after the CAD processing. The radiographic image 30BP after the CAD processing or the radiographic image 30CP after the CAD processing is output from the CAD processing unit 50 to the RW control unit 81 and is stored in the storage device 61 by the RW control unit 81 (Step ST350).

The radiographic image 30BP after the CAD processing or the radiographic image 30CP after the CAD processing is read out from the storage device 61 by the RW control unit 81 and is output to the return unit 84. The radiographic image 30BP after the CAD processing or the radiographic image 30CP after the CAD processing is returned as the CAD processing result 58 to the console 13B or the console 13C by the return unit 84 (Step ST360, the return processing).

In a case where the acceptability inquiry 55 is received while the second reception processing, the second CAD processing, and the return processing on any one of the radiographic image 30B or the radiographic image 30C are being executed, as shown in FIG. 12, the first busy state notification 110, instead of the acceptability notification 56, is notified from the notification unit 78 to the console 13B or the console 13C. With the reception of the first busy state notification 110, the first busy state notification screen 115 shown in FIG. 13 is displayed on the display of the console 13B or the console 13C.

After the return processing, as shown in FIG. 17, the radiographic image 30B or the radiographic image 30C and the radiographic image 30BP after the CAD processing or the radiographic image 30CP after the CAD processing of the storage device 61 are erased by the RW control unit 81 (Step ST370, the erasure processing). Wireless transmission (the first notification processing) of the acceptability notification 56 by the notification unit 78 is resumed (Step ST370).

As described above, the CPU 63 of the radiation generation apparatus 11A comprises the first reception unit 79, the second reception unit 80, and the return unit 84. The GPU 64 comprises the CAD processing unit 50. The first reception unit 79 executes first reception processing of receiving the radiographic image 30A from the electronic cassette 12A. The second reception unit 80 executes the second reception processing of receiving the radiographic image 30B from the radiography system 10B or the radiographic image 30C from the radiography system 10C. The CAD processing unit 50 executes the first CAD processing of executing the CAD processing on the radiographic image 30A. The CAD processing unit 50 executes the second CAD processing of executing the CAD processing on the radiographic image 30B or the radiographic image 30C. The return unit 84 executes the return processing of returning the CAD processing result 58 as a result of the second CAD processing to the radiography system 10B or the radiography system 10C. In this way, since the target of the CAD processing by the CAD processing unit 50 is not limited to the radiographic image 30A, the radiation generation apparatus 11A can effectively utilize the function of the CAD processing.

The notification unit 78 executes the first notification processing of notifying the radiography system 10B or the radiography system 10C that the request of the second CAD processing can be accepted, with the acceptability notification 56. For this reason, the operator of the radiography system 10B or the radiography system 10C can be informed of the presence of the radiography system 10A that can accept the request of the second CAD processing.

The RW control unit 81 executes the erasure processing of erasing the radiographic image 30B or the radiographic image 30C and the radiographic image 30BP after the CAD processing or the radiographic image 30CP after the CAD processing from the storage device 61 after the return processing by the return unit 84.

Since the radiation generation apparatus 11A is a "mobile radiation generation apparatus", the radiation generation apparatus 11A has many chances to be exposed to a person other than the operator OP compared to a stationary type radiation generation apparatus. For this reason, there is a need to further improve the data security of the "second radiographic image" as an article on deposit from another radiography system. In the technique of the present disclosure, a configuration is made in which the "second radiographic image" is stored in the storage device 61 for a required period and is erased from the storage device 61 in a case where the "second radiographic image" is no longer required. Accordingly, it is possible to reduce a concern that the "second radiographic image" leaks from the radiation generation apparatus 11A, and to contribute to the improvement of the data security of the "second radiographic image".

The notification unit 78 executes the first restriction processing of interrupting the first notification processing while the second reception processing, the second CAD processing, and the return processing on one "second radiographic image" are being executed, such that only one "second radiographic image" is present in the radiation generation apparatus 11A. For this reason, it is possible to reliably restrain a mistake, such as erroneously returning the CAD processing result 58 including the radiographic image 30BP after the CAD processing to the console 13C or erroneously returning the CAD processing result 58 including the radiographic image 30CP after the CAD processing to the console 13B. Accordingly, even with this configuration, it is possible to contribute to the improvement of the data security of the "second radiographic image".

The notification unit 78 executes the second notification processing of notifying the radiography system 10B or the radiography system 10C that the second reception processing, the second CAD processing, and the return processing on one "second radiographic image" are being executed, with the first busy state notification 110. For this reason, it is possible to reliably inform the operator of the radiography system 10B or the radiography system 10C that the second reception processing, the second CAD processing, and the return processing on one "second radiographic image" are being executed in the radiation generation apparatus 11A, and the radiation generation apparatus 11A is not in a state of receiving the request of the CAD processing.

As shown in FIG. 16, the transfer speed at which the radiographic image 30B or the radiographic image 30C received in the second reception processing is transferred to the second CAD processing is faster than the transmission speed of the radiographic image 30B from the radiography system 10B and the transmission speed of the radiographic image 30C from the radiography system 10C. For this reason, it is possible to start the second CAD processing without delay after the radiographic image 30B or the radiographic image 30C is received in the second reception processing.

The radiation generation apparatus 11A has the CPU 63 that executes the processing other than the first CAD processing and the second CAD processing, and the GPU 64 that executes at least the first CAD processing and the second CAD processing.

Since the CAD processing has a comparatively large processing load, in a case where the CAD processing and other kinds of processing are executed in parallel with one processor, a processing speed of each of the CAD processing and other kinds of processing may be temporarily delayed. In contrast, in the technique of the present disclosure, as described above, the processor is divided into the CPU 63 that executes the processing other than the first CAD processing and the second CAD processing, and the GPU 64 that executes at least the first CAD processing and the second CAD processing. Accordingly, it is possible to execute the first CAD processing and the second CAD processing at a high speed without influencing on other kinds of processing.

The notification unit 78 executes the second restriction processing of interrupting the first notification processing while the imaging-related processing involving imaging of the radiographic image 30A and including the first reception processing and the first CAD processing is being executed, not to execute the second CAD processing. For this reason, it is possible to give priority to the imaging-related processing of the radiography system 10A over the second CAD processing that is additional processing for the radiography system 10A.

The notification unit 78 executes the third notification processing of notifying the radiography system 10B or the radiography system 10C that the imaging-related processing is being executed, by the second busy state notification 120. For this reason, it is possible to reliably inform the operator of the radiography system 10B or the radiography system 10C that the imaging-related processing is being executed in the radiation generation apparatus 11A, and the radiation generation apparatus 11A is not in a state of receiving the request of the CAD processing.

In the first notification processing is interrupted in the notification unit 78, a communication establishment state of the console 13B and the console 13C by the wireless communication unit 60 may be maintained until the first notification processing is resumed. On the contrary, in a case where the first notification processing is interrupted in the notification unit 78, the communication establishment state of the console 13B and the console 13C by the wireless communication unit 60 may also be cancelled. In this case, the wireless communication unit 60 executes processing of establishing communication with the console 13B or the console 13C again at the time of resuming the first notification processing.

Figure 20:
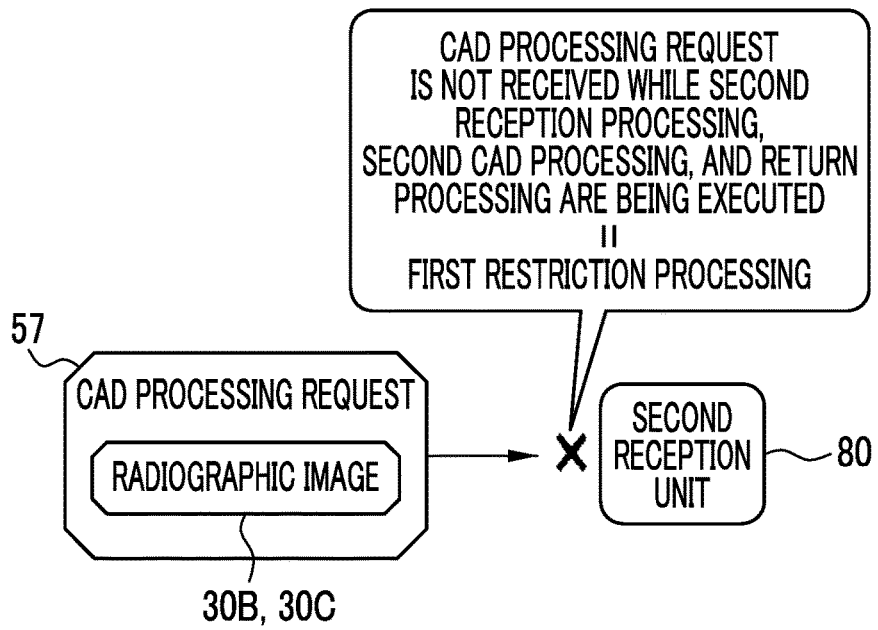
FIG. 20 is a diagram showing another example of first restriction processing.
Figure 21:
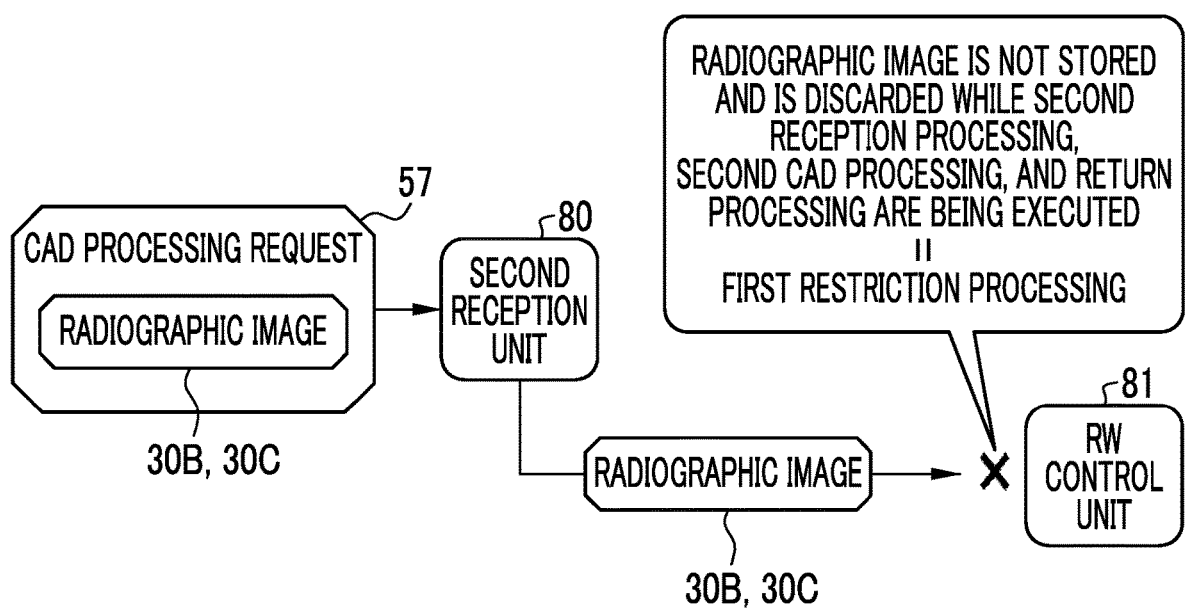
FIG. 21 is a diagram showing still another example of first restriction processing.

The first restriction processing is not limited to the above-described aspect where the first notification processing is interrupted. Instead of interrupting the first notification processing, first restriction processing based on an aspect described below may be executed. For example, as shown in FIG. 20, an aspect may be made in which the CAD processing request 57 is not received in the second reception unit 80 while the second reception processing, the second CAD processing, and the return processing on any one of the radiographic image 30B or the radiographic image 30C are being executed. Alternatively, as shown in FIG. 21, an aspect may be made in which the radiographic image 30B or the radiographic image 30C that is included in the CAD processing request 57 received in the second reception unit 80 is not stored in the storage device 61 and is discarded while the second reception processing, the second CAD processing, and the return processing on any one of the radiographic image 30B or the radiographic image 30C are being executed. Even with the aspects shown in FIGS. 20 and 21, it is possible to contribute to the improvement of the data security of the "second radiographic image".

Even in the aspects shown in FIGS. 20 and 21, the notification unit 78 notifies the console 13B or the console 13C of the first busy state notification 110 indicating that the second reception processing, the second CAD processing, and the return processing on one "second radiographic image" are being executed.

As the first restriction processing, an aspect where, in a case where the CAD processing request 57 is received from one of the console 13B and console 13C, the communication establishment state with the other console of the console 13B and the console 13C is cancelled, and only the communication establishment state with one of the console 13B and the console 13C is maintained may be employed.

Figure 22:
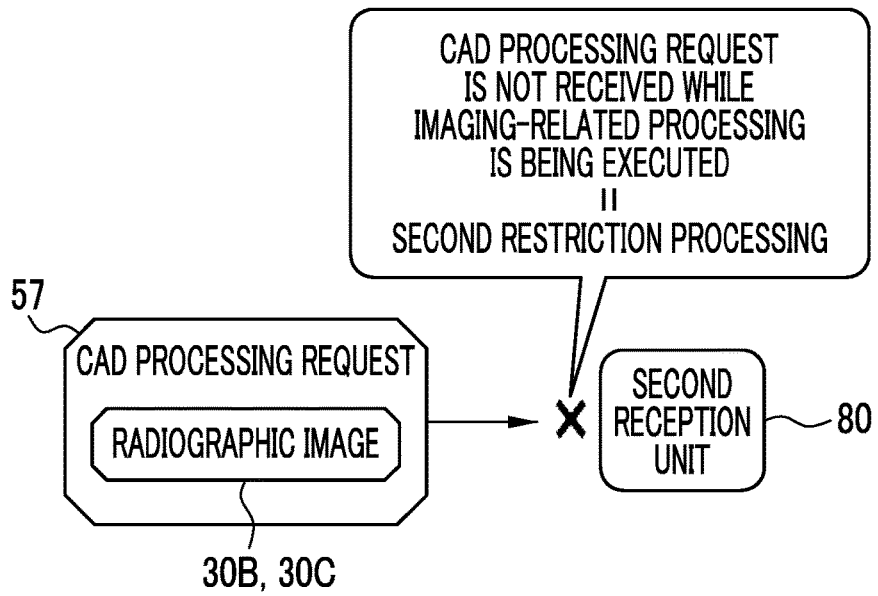
FIG. 22 is a diagram showing another example of second restriction processing.
Figure 23:
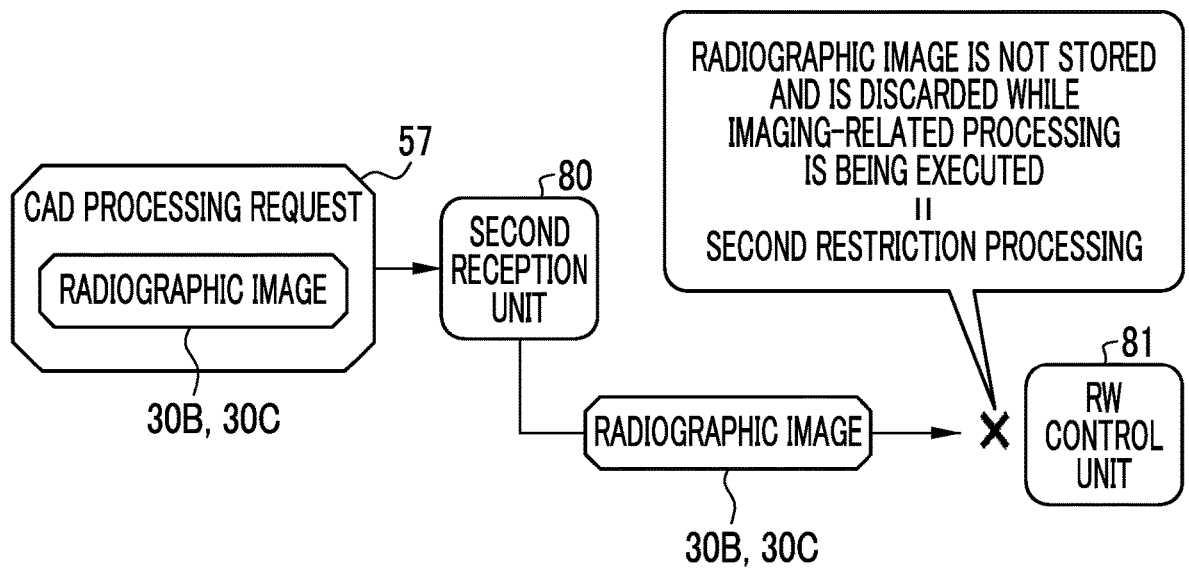
FIG. 23 is a diagram showing still another example of second restriction processing.

Similarly to the first restriction processing, the second restriction processing is also not limited to the above-described aspect where the first notification processing is interrupted. Instead of interrupting the first notification processing, second restriction processing based on an aspect described below may be executed. For example, as shown in FIG. 22, an aspect may be made in which the CAD processing request 57 is not received in the second reception unit 80 while the imaging-related processing is being executed. Alternatively, as shown in FIG. 23, an aspect may be made in which the radiographic image 30B or the radiographic image 30C that is included in the CAD processing request 57 received in the second reception unit 80 is not stored in the storage device 61 and is discarded while the imaging-related processing is being executed. Even with the aspects shown in FIGS. 22 and 23, the radiography system 10A can give priority to the imaging-related processing of the radiography system 10A.

Even in the aspects shown in FIGS. 22 and 23, the notification unit 78 notifies the console 13B or the console 13C of the second busy state notification 120 indicating that the imaging-related processing is being executed.

In the above-described embodiment, although an example where one radiation generation apparatus 11A that is an example of a "mobile radiation generation apparatus" according to the technique of the present disclosure is provided has been described, the technique of the present disclosure is not limited thereto. A plurality of "mobile radiation generation apparatuses" may be provided. In this case, on the acceptability notification screen 105, a plurality of request buttons 107 corresponding to a plurality of "mobile radiation generation apparatuses" are displayed in an alternatively selectable form.

Similarly, the "second radiography system" is not limited to the two radiography systems of the radiography system 10B and the radiography system 10C illustrated in the drawing. Two or more "second radiography systems" may be provided.

The CAD processing result 58 is not limited to the radiographic image 30BP after the CAD processing or the radiographic image 30CP after the CAD processing illustrated in the drawing. Information regarding a display position of the marker 100 surrounding the candidate of the lesion extracted by the second CAD processing may be returned as CAD processing result 58. In a case where no candidate of a lesion is extracted, information indicating that no candidate of a lesion is extracted may be returned as CAD processing result 58.

In addition to the radiation generation apparatus 11A, an apparatus (hereinafter, referred to as a CAD processing apparatus) that executes second CAD processing on the radiographic image 30B or the radiographic image 30C may be present on the network. In this case, as a situation in which the second CAD processing is requested from the radiography system 10B or the radiography system 10C to the radiation generation apparatus 11A, not to the CAD processing apparatus, for example, the following situations are considered. First, there is a case where a function of CAD processing in the CAD processing apparatus fails and cannot be used. Second, there is a case where a network failure occurs due to a disaster or the like, and the console 13B or the console 13C and the CAD processing apparatus cannot perform communication.

Figure 24:
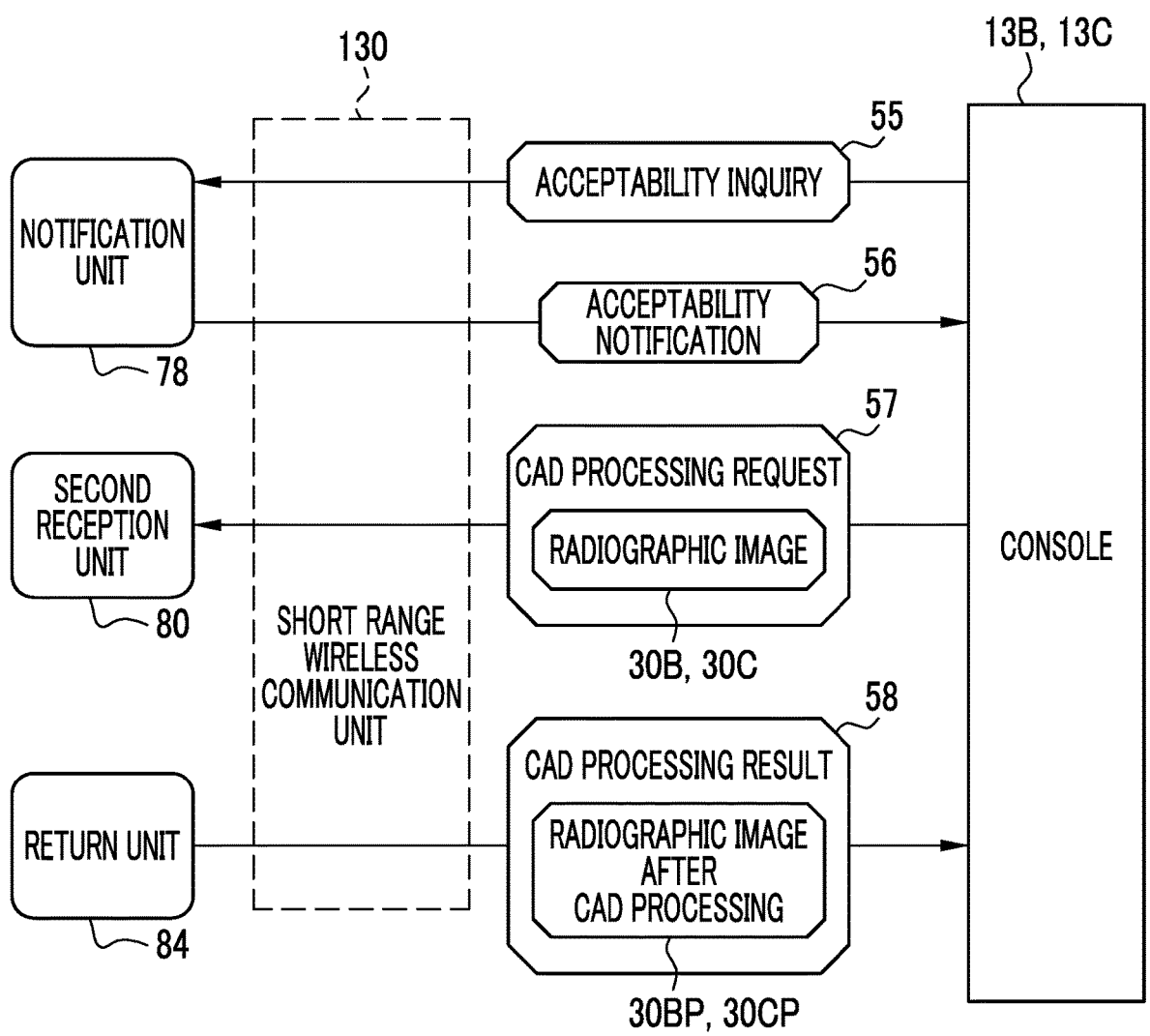
FIG. 24 is a diagram showing an aspect where the second reception processing and the return processing are executed through short range wireless communication.

As a countermeasure of the second case, for example, the following countermeasure is considered. First, as shown in FIG. 24, the reception of the acceptability inquiry 55 and the transmission of the acceptability notification 56 by the notification unit 78, the reception of the CAD processing request 57 by the second reception unit 80, and the transmission of the CAD processing result 58 by the return unit 84 are performed through a short range wireless communication unit 130. That is, the second reception processing and the return processing are configured as processing of receiving and returning the radiographic image 30B or the radiographic image 30C through short range wireless communication. The short range wireless communication unit 130 performs transmission and reception of each kind of information described above, for example, conforming to a short range wireless communication standard, such as Bluetooth (Registered Trademark) or ZigBee (Registered Trademark).

Figure 25:
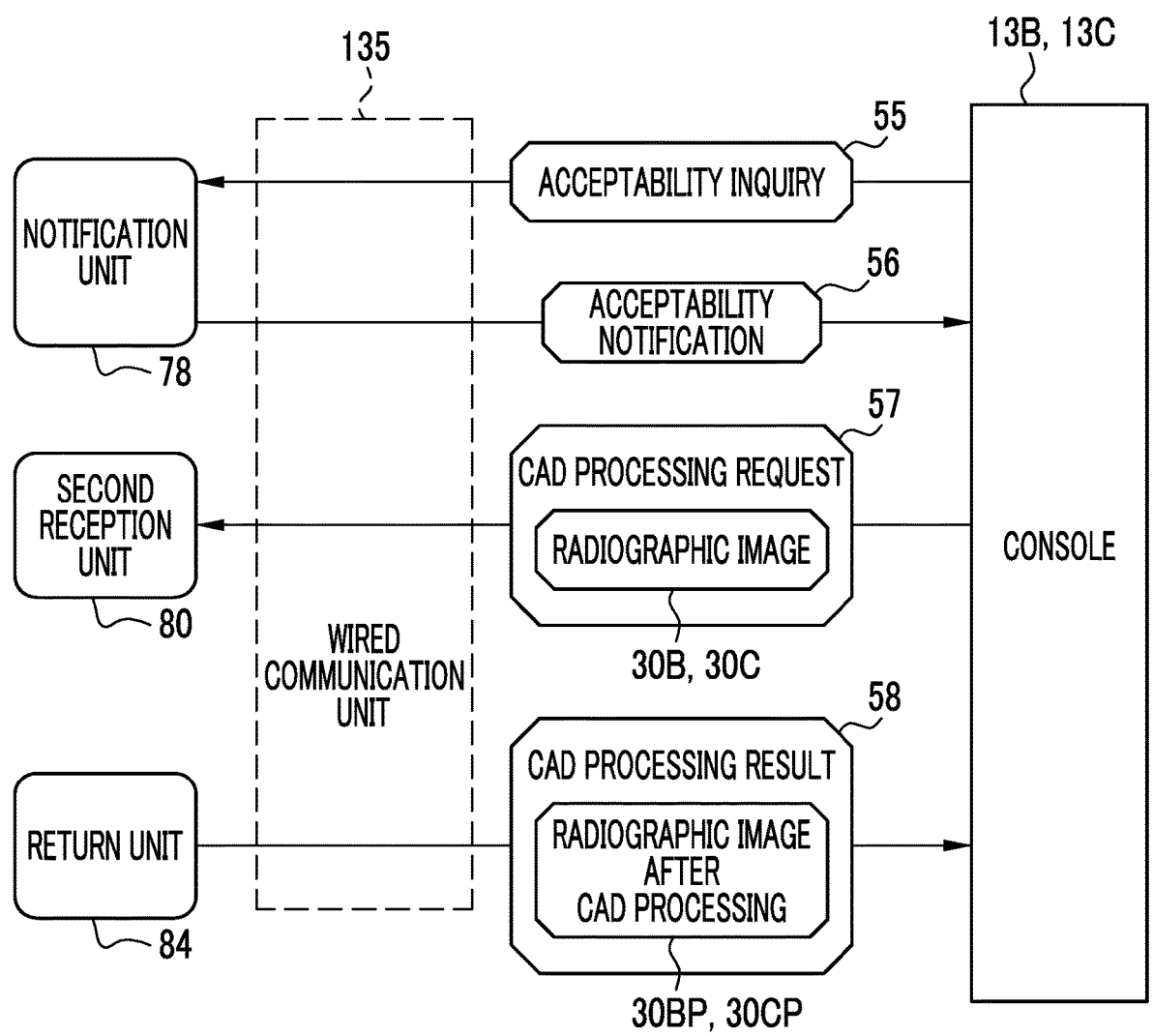
FIG. 25 is a diagram showing an aspect where the second reception processing and the return processing are executed through wired communication.

Alternatively, as shown in FIG. 25, the reception of the acceptability inquiry 55 and the transmission of the acceptability notification 56 by the notification unit 78, the reception of the CAD processing request 57 by the second reception unit 80, and the transmission of the CAD processing result 58 by the return unit 84 are performed through a wired communication unit 135. That is, the second reception processing and the return processing are configured as processing of receiving and returning the radiographic image 30B or the radiographic image 30C through wired communication. The wired communication unit 135 performs transmission and reception of each kind of information described above, for example, conforming to a wired communication standard, such as a universal serial bus (USB) standard.

In this way, in a case where the second reception processing and the return processing are configured as processing using short range wireless communication or wired communication, even in a case where a network failure occurs and communication with the CAD processing apparatus cannot be performed, the second CAD processing on the radiographic image 30B or the radiographic image 30C can be executed.

The wireless communication unit 60 shown in FIG. 6 and at least one the short range wireless communication unit 130 shown in FIG. 24 or the wired communication unit 135 shown in FIG. 25 may be provided. The wireless communication unit 60 may be used normally, and in a case where a network failure occurs, the communication unit may be switched to the short range wireless communication unit 130 or the wired communication unit 135.

In the above-described embodiment, although the CAD processing unit 50 executes the CAD processing using the model 72 for CAD processing, the technique of the present disclosure is not limited thereto. The CAD processing may be executed using a known image recognition technique.

In the above-described embodiment, although the CAD processing is automatically executed on the radiographic image 30A in the CAD processing unit 50 when the set time has elapsed after the radiographic image 30A is displayed on the display 42, the technique of the present disclosure is not limited thereto. Only in a case where there is an instruction of the operator OP, the CAD processing may be executed on the radiographic image 30A.

There may be plurality of kinds of CAD processing that can be executed by the CAD processing unit 50. In this case, on the acceptability notification screen 105, in addition to the request button 107, a graphical user interface (GUI) for instructing execution of desire CAD processing among a plurality of kinds of CAD processing is displayed.

The GPU 64 may have the functions of the image processing unit 82, the display control unit 83, and the like in addition to the CAD processing unit 50.

In the above-described embodiment, although the imaging-related processing is started in a case where the warm-up instruction signal 92 is received in the reception unit 75, the technique of the present disclosure is not limited thereto. In a case where the operator OP selects the imaging menu 90, the imaging-related processing may be started. Alternatively, in a case where the irradiation start instruction signal 93 is received in the reception unit 75, the imaging-related processing may be started. In addition, in a case where the radiographic image 30A is received in the first reception unit 79, the imaging-related processing may be started.

Similarly, the end of the imaging-related processing is not limited to a case where the first CAD processing ends. In a case where the radiographic image 30AP after the CAD processing is displayed on the display 42 by the display control unit 83, the imaging-related processing may end. In conclusion, the imaging-related processing may include at least the first reception processing and the first CAD processing.

In the above-described embodiment, although the first restriction processing ends conforming to the end timing of the return processing, the technique of the present disclosure is not limited thereto. The first restriction processing may be extended and executed until an end timing of the erasure processing.

In the above-described embodiment, although the electronic cassette 12A that performs the accumulation operation in response to the irradiation start synchronization signal 94 and performs the readout operation in response to the irradiation end synchronization signal 95 has been illustrated, the technique of the present disclosure is not limited thereto. An electronic cassette having a function of detecting the irradiation start and the irradiation end of the radiation R by itself may be used.

In the above-described embodiment, for example, as the hardware structure of processing units that execute various kinds of processing, such as the CAD processing unit 50, the reception unit 75, the irradiation control unit 76, the cassette control unit 77, the notification unit 78, the first reception unit 79, the second reception unit 80, the RW control unit 81, the image processing unit 82, the display control unit 83, and the return unit 84, various processors described below can be used. Various processors include a programmable logic device (PLD) that is a processor capable of changing a circuit configuration after manufacture, such as a field programmable gate array (FPGA), a dedicated electric circuit that is a processor having a circuit configuration dedicatedly designed for executing specific processing, such as an application specific integrated circuit (ASIC), and the like in addition to the CPU 63 and the GPU 64 that are general-purpose processors configured to execute software (operation program 70) to function as various processing units, as described above.

One processing unit may be configured of one of various processors described above or may be configured of a combination of two or more processors (for example, a combination of a plurality of FPGAs and/or a combination of a CPU and an FPGA) of the same type or different types. A plurality of processing units may be configured of one processor.

As an example where a plurality of processing units are configured of one processor, first, as represented by a computer, such as a client or a server, there is a form in which one processor is configured of a combination of one or more CPUs and software, and the processor functions as a plurality of processing units. Second, as represented by system on chip (SoC) or the like, there is a form in which a processor that implements all functions of a system including a plurality of processing units into one integrated circuit (IC) chip is used. In this way, various processing units may be configured using one or more processors among various processors described above as a hardware structure.

In addition, as the hardware structure of various processors, more specifically, an electric circuit (circuitry), in which circuit elements, such as semiconductor elements, are combined, can be used.

The technique of the present disclosure can also be appropriately combined with various embodiments and/or various modification examples described above. The technique of the present disclosure is not limited to the above-described embodiments, and various configurations can be of course employed without departing from the spirit and scope of the technique of the present disclosure. In addition to the program, the technique of the present disclosure extends to a storage medium that stores the program in a non-transitory manner. The content of the above description and the content of the drawings are detailed description of portions according to the technique of the present disclosure, and are merely examples of the technique of the present disclosure. For example, the above description relating to configuration, function, operation, and advantageous effects is description relating to examples of configuration, function, operation, and advantageous effects of the portions according to the technique of the present disclosure. Thus, it is needless to say that unnecessary portions may be deleted, new elements may be added, or replacement may be made to the content of the above description and the content of the drawings without departing from the gist of the technique of the present disclosure. Furthermore, to avoid confusion and to facilitate understanding of the portions according to the technique of the present disclosure, description relating to common technical knowledge and the like that does not require particular description to enable implementation of the technique of the present disclosure is omitted from the content of the above description and the content of the drawings.

In the specification, "A and/or B" is synonymous with "at least one of A or B". That is, "A and/or B" may refer to A alone, B alone, or a combination of A and B. Furthermore, in the specification, a similar concept to "A and/or B" applies to a case in which three or more matters are expressed by linking the matters with "and/or".

All of the documents, patent applications, and technical standards in the specification are incorporated herein by reference to the same extent that the individual documents, patent applications, and technical standards are described specifically and independently.

What is claimed is:

1. A mobile radiation generation apparatus that is used for a first radiography system configured to capture a first radiographic image, has a radiation generation unit including a radiation tube configured to emit radiation, is movable with a carriage having wheels, and is driven with a battery, the mobile radiation generation apparatus comprising:
at least one processor configured to execute
a first reception process of receiving the first radiographic image,
a first computer aided diagnosis process of executing computer aided diagnosis processing on the first radiographic image,
a second reception process of receiving a second radiographic image from a second radiography system different from the first radiography system,
a second computer aided diagnosis process of executing the computer aided diagnosis processing on the second radiographic image, and
a return process of returning a result of the second computer aided diagnosis process to the second radiography system.

2. The mobile radiation generation apparatus according to claim 1,
wherein the at least one processor is configured to execute a first notification process of notifying the second radiography system that a request for the second computer aided diagnosis process is acceptable.

3. The mobile radiation generation apparatus according to claim 1,
wherein the at least one processor is configured to execute an erasure process of erasing the second radiographic image from a storage unit after the return process.

4. The mobile radiation generation apparatus according to claim 1,
wherein the at least one processor is configured to execute a first restriction process of bringing the mobile radiation generation apparatus into a state in which only one second radiographic image is present while the second reception process, the second computer aided diagnosis process, and the return process on one second radiographic image are being executed.

5. The mobile radiation generation apparatus according to claim 4,
wherein the at least one processor is configured to execute a second notification process of notifying the second radiography system that the second reception process, the second computer aided diagnosis process, and the return process on the one second radiographic image are being executed.

6. The mobile radiation generation apparatus according to claim 1,
wherein a transfer speed at which the second radiographic image received in the second reception process is transferred to the second computer aided diagnosis process is faster than a transmission speed of the second radiographic image from the second radiography system.

7. The mobile radiation generation apparatus according to claim 1,
wherein the at least one processor has
a first sub-processor that executes a process other than the first computer aided diagnosis process and the second computer aided diagnosis process, and
a second sub-processor that executes at least the first computer aided diagnosis process and the second computer aided diagnosis process.

8. The mobile radiation generation apparatus according to claim 1,
wherein the at least one processor is configured to execute a second restriction process of not executing the second computer aided diagnosis process while an imaging-related process involving imaging of the first radiographic image and including the first reception process and the first computer aided diagnosis process is being executed.

9. The mobile radiation generation apparatus according to claim 8,
wherein the at least one processor is configured to execute a third notification process of notifying the second radiography system that the imaging-related process is being executed.

10. The mobile radiation generation apparatus according to claim 1,
wherein the second reception process and the return process are processes of receiving and returning the second radiographic image through short range wireless communication or wired communication.

11. A method for operating a mobile radiation generation apparatus that is used for a first radiography system configured to capture a first radiographic image, has a radiation generation unit including a radiation tube configured to emit radiation, is movable with a carriage having wheels, and is driven with a battery, the method causing a processor of a computer to execute:
a first reception process of receiving the first radiographic image,
a first computer aided diagnosis process of executing computer aided diagnosis processing on the first radiographic image,
a second reception process of receiving a second radiographic image from a second radiography system different from the first radiography system,
a second computer aided diagnosis process of executing the computer aided diagnosis processing on the second radiographic image, and
a return process of returning a result of the second computer aided diagnosis process to the second radiography system.

12. A non-transitory computer-readable storage medium storing an operation program for a mobile radiation generation apparatus that is used for a first radiography system configured to capture a first radiographic image, has a radiation generation unit including a radiation tube configured to emit radiation, is movable with a carriage having wheels, and is driven with a battery, the operation program causing a processor of a computer to execute:
a first reception process of receiving the first radiographic image,
a first computer aided diagnosis process of executing computer aided diagnosis processing on the first radiographic image,
a second reception process of receiving a second radiographic image from a second radiography system different from the first radiography system,
a second computer aided diagnosis process of executing the computer aided diagnosis processing on the second radiographic image, and
a return process of returning a result of the second computer aided diagnosis process to the second radiography system.

* * * * *